US009752164B2

(12) United States Patent
Razavi-Shirazi et al.

(10) Patent No.: US 9,752,164 B2
(45) Date of Patent: Sep. 5, 2017

(54) ENHANCED EFFICIENCY ETHANOL AND SUGAR CONVERSION PROCESSES

(71) Applicant: Microvi Biotech Inc., Hayward, CA (US)

(72) Inventors: Fatemeh Razavi-Shirazi, Hayward, CA (US); Ameen Razavi, Fremont, CA (US); Norman Louis Balmer, Ridgefield, CT (US)

(73) Assignee: MICROVI BIOTECH, INC., Hayward, CA (US)

( * ) Notice: Subject to any disclaimer, the term of this patent is extended or adjusted under 35 U.S.C. 154(b) by 0 days.

(21) Appl. No.: 13/918,838

(22) Filed: Jun. 14, 2013

(65) Prior Publication Data

US 2013/0337517 A1    Dec. 19, 2013

Related U.S. Application Data

(60) Provisional application No. 61/689,941, filed on Jun. 15, 2012, provisional application No. 61/689,944, filed on Jun. 15, 2012, provisional application No. 61/689,948, filed on Jun. 15, 2012.

(51) Int. Cl.
  *C12P 7/14* (2006.01)
  *C12N 11/04* (2006.01)
  *C12N 11/08* (2006.01)
  *C12P 7/10* (2006.01)

(52) U.S. Cl.
  CPC ............... *C12P 7/14* (2013.01); *C12N 11/04* (2013.01); *C12N 11/08* (2013.01); *C12P 7/10* (2013.01); *C12P 2203/00* (2013.01); *Y02E 50/16* (2013.01)

(58) Field of Classification Search
  None
  See application file for complete search history.

(56) References Cited

U.S. PATENT DOCUMENTS

| 3,767,790 A | 10/1973 | Guttag |
| 4,148,689 A | 4/1979 | Hino et al. |
| 4,195,129 A | 3/1980 | Fukui et al. |
| 4,250,264 A | 2/1981 | Nelson et al. |
| 4,287,305 A | 9/1981 | Compere et al. |
| 4,352,883 A | 10/1982 | Lim |
| 4,450,233 A | 5/1984 | Mimura et al. |
| 4,469,600 A | 9/1984 | Frydman et al. |
| 4,524,137 A | 6/1985 | Hagerdal et al. |
| 4,546,081 A | 10/1985 | Yamada et al. |

(Continued)

FOREIGN PATENT DOCUMENTS

JP          10-314782          12/1998

OTHER PUBLICATIONS

Barcina et al., "The Viable but Nonculturable Phenotype: A Crossroads in the Life-Cycle of Non-Differentiating Bacteria?," Rev Environ Sci Biotechnol (2009) vol. 8, pp. 245-255.

(Continued)

*Primary Examiner* — Blaine Lankford
*Assistant Examiner* — Lauren K Van Buren
(74) *Attorney, Agent, or Firm* — Dentons US LLP

(57) ABSTRACT

Overlay processes are disclosed for making ethanol that not only increase ethanol conversion but do so in a cost effective manner with a reduction in energy requirements per unit of ethanol production. The processes can provide, if desired, higher organic compound as a co-product with ethanol.

5 Claims, 2 Drawing Sheets

(56) References Cited

U.S. PATENT DOCUMENTS

| | | | |
|---|---|---|---|
| 4,647,536 A | 3/1987 | Mosbach et al. | |
| 4,659,664 A | 4/1987 | de Buda | |
| 4,727,030 A | 2/1988 | Ishimura et al. | |
| 4,774,178 A | 9/1988 | Egerer et al. | |
| 4,791,061 A | 12/1988 | Sumino et al. | |
| 4,816,399 A | 3/1989 | Lawford | |
| 4,921,803 A | 5/1990 | Nohr | |
| 4,950,596 A | 8/1990 | Cheng et al. | |
| 4,975,375 A | 12/1990 | Haruta et al. | |
| 5,034,324 A | 7/1991 | Shinozaki et al. | |
| 5,071,747 A | 12/1991 | Hough et al. | |
| 5,089,407 A | 2/1992 | Baker et al. | |
| 5,100,673 A | 3/1992 | Bader et al. | |
| 5,112,750 A | 5/1992 | Tanaka et al. | |
| 5,137,818 A | 8/1992 | Harder et al. | |
| 5,279,745 A | 1/1994 | Jeffers et al. | |
| 5,290,693 A | 3/1994 | Chen et al. | |
| 5,324,445 A | 6/1994 | Langley et al. | |
| 5,439,859 A | 8/1995 | Durante et al. | |
| 5,462,866 A | 10/1995 | Wang | |
| 5,486,292 A | 1/1996 | Bair et al. | |
| 5,541,234 A | 7/1996 | Unger et al. | |
| 5,595,893 A | 1/1997 | Pometto, III et al. | |
| 5,620,883 A | 4/1997 | Shao et al. | |
| 5,840,338 A | 11/1998 | Roos et al. | |
| 5,906,828 A | 5/1999 | Cima et al. | |
| 6,077,432 A | 6/2000 | Coppola et al. | |
| 6,133,004 A | 10/2000 | Sato et al. | |
| 6,139,963 A | 10/2000 | Fujii et al. | |
| 6,153,416 A | 11/2000 | Yuan | |
| 6,214,619 B1 | 4/2001 | Sato et al. | |
| 6,258,870 B1 | 7/2001 | Hubbell et al. | |
| 6,337,019 B1 | 1/2002 | Razavi-Shirazi | |
| 6,395,521 B1 | 5/2002 | Miura | |
| 6,395,522 B1 | 5/2002 | DeFilippi et al. | |
| 6,610,205 B2 | 8/2003 | Sato et al. | |
| 6,855,513 B1 | 2/2005 | Whiteley et al. | |
| 7,060,185 B2 | 6/2006 | Kim et al. | |
| 7,297,236 B1 | 11/2007 | Vander Griend | |
| 7,384,777 B2 | 6/2008 | Willuweit et al. | |
| 7,556,961 B2 | 7/2009 | Isaka et al. | |
| 7,704,733 B2 | 4/2010 | Sumino et al. | |
| 7,794,590 B2 | 9/2010 | Yoshikawa et al. | |
| 7,816,110 B2 | 10/2010 | Aoyama et al. | |
| 7,842,185 B2 | 11/2010 | Abe et al. | |
| 7,888,062 B1 | 2/2011 | Garner et al. | |
| 7,931,807 B2 | 4/2011 | Bowman | |
| 8,227,226 B2 | 7/2012 | Kitasaki et al. | |
| 8,241,890 B2 | 8/2012 | Stloukal | |
| 8,293,510 B2 | 10/2012 | Detamore et al. | |
| 2002/0164364 A1 | 11/2002 | Quong | |
| 2004/0253696 A1 | 12/2004 | Grichko | |
| 2005/0037082 A1 | 2/2005 | Wan et al. | |
| 2005/0269261 A1 | 12/2005 | Sublette | |
| 2008/0044891 A1* | 2/2008 | Kinley et al. | 435/289.1 |
| 2009/0061499 A1* | 3/2009 | Stloukal et al. | 435/182 |
| 2009/0093027 A1 | 4/2009 | Balan et al. | |
| 2009/0155414 A1 | 6/2009 | Abbas et al. | |
| 2009/0203098 A1 | 8/2009 | Verser | |
| 2009/0203103 A1 | 8/2009 | Pierce et al. | |
| 2009/0227004 A1 | 9/2009 | Dale | |
| 2009/0258051 A1* | 10/2009 | Chidambaram et al. | 424/423 |
| 2009/0258404 A1 | 10/2009 | Mikkelsen et al. | |
| 2010/0133114 A1 | 6/2010 | Bukshpan et al. | |
| 2010/0230348 A1 | 9/2010 | Isaka et al. | |
| 2010/0233771 A1* | 9/2010 | McDonald et al. | 435/161 |
| 2010/0285552 A1 | 11/2010 | Varanasi et al. | |
| 2010/0330633 A1 | 12/2010 | Walther et al. | |
| 2011/0006000 A1 | 1/2011 | Post et al. | |
| 2011/0008489 A1 | 1/2011 | Robb et al. | |
| 2011/0039317 A1* | 2/2011 | Medoff | 435/155 |
| 2011/0053236 A1 | 3/2011 | Walmsley et al. | |
| 2011/0129887 A1 | 6/2011 | Contag et al. | |
| 2011/0130586 A1 | 6/2011 | Reaney et al. | |
| 2011/0152176 A1 | 6/2011 | Horswill | |
| 2011/0186508 A1 | 8/2011 | Bowman | |
| 2011/0207191 A1 | 8/2011 | Um et al. | |
| 2011/0233125 A1 | 9/2011 | Jones et al. | |
| 2012/0115045 A1 | 5/2012 | Kapopara et al. | |
| 2012/0142531 A1 | 6/2012 | Mazeaud et al. | |
| 2012/0208255 A1 | 8/2012 | Andersen et al. | |
| 2012/0308632 A1 | 12/2012 | Ghigo et al. | |
| 2013/0022578 A1 | 1/2013 | Newman et al. | |
| 2013/0023035 A1 | 1/2013 | Bielinski et al. | |
| 2013/0023053 A1 | 1/2013 | March et al. | |
| 2013/0034907 A1 | 2/2013 | Collins et al. | |
| 2013/0035513 A1 | 2/2013 | Hu et al. | |
| 2013/0210101 A1 | 8/2013 | Parekh et al. | |

OTHER PUBLICATIONS

Ben-Jacob et al., "Self-Engineering Capabilities of Bacteria," J. R. Soc. Interface, (2006), vol. 3, pp. 197-214.

Chen et al., "Surface hydration: Principles and Applications Toward Low-Fouling/Nonfouling Biomaterials," Polymer 51, (2010), pp. 5283-5293.

Cho et al., "Self-Organization in High-Density Bacterial Colonies: Efficient Crowd Control," PLoS Biology, Nov. 2007, vol. 5, Issue 11, pp. 2614-2623.

Choi et al., "Engineered Materials and the Cellular Microenvironment: A Strengthening Interface Between Cell Biology and Bioengineering," Trends in Cell Biology, Dec. 2010, vol. 20, No. 12, pp. 705-714.

Christensson et al., "ANITA™ Mox—A BioFarm Solution for Fast Start-up of Deammonifying MBBRs," Sweden, WEFTEC. 2011, 18 pages.

Dawson et al., ""Persisters": Survival at the Cellular Level," PLoS Pathogens, Jul. 2011, vol. 7, Issue 7, pp. 1-3.

Delaittre et al., "Chemical Approaches to Synthetic Polymer Surface Biofunctionalization for Targeted Cell Adhesion Using Small Binding Motifs," Soft Matter, 2012, vol. 8, pp. 7323-7347.

Donlan, Rodney M., "Biofilms: Microbial Life on Surfaces," Emerging Infectious Diseases, vol. 8, No. 9, Sep. 2002, pp. 881-890.

Dunlop, Mary J., "Engineering Microbes for Tolerance to Next-Generation Biofuels," Dunlop Biotechnology for Biofuels, 2011, vol. 4, No. 32, pp. 1-9.

Entry et al., "Polyacrylamide Removes Microorganisms and Nutrients from Surface Water," USDA, Northwest Irrigation & Soils Research Lab, Kimberly, ID, 9 pages.

Joshi et al., "Effect of Molecular Weight on Dielectric Properties of Polyvinyl Alcohol Films," J. Appl. Polum. Sci., 102, 2006, pp. 1014-1016.

Kato et al., "Microbial Interspecies Electron Transfer via Electric Currents Through Conductive Minerals," PNAS Early Edition, pp. 1-5.

Katsikogianni et al., "Concise Review of Mechanisms of Bacterial Adhesion to Biomaterials and of Techniques Used in Estimating Bacteria-Material Interactions," Laboratory of Biomechanics and Biomedical Engineering, European Cells and Materials, vol. 8, 2004, pp. 34-57.

Kharkar et al., "Designing Degradable Hydrogels for Orthogonal Control of Cell Microenvironments," Chem. Soc. Rev., (2013), vol. 42, pp. 7335-7372.

Manina et al., "A Single-Cell Perspective on Non-Growing but Metabolically Active (NGMA) Bacteria," Current Topics in Microbiology and Immunology, (2013), 27 pages.

Mukamolova et al., "Adoption of the Transiently Non-Culturable State—a Bacterial Survival Strategy?," Advances in Microbial Physiology, (2003) vol. 47, pp. 65-129.

Nagadomi et al., "Treatment of Aquarium Water by Denitrifying Photosynthetic Bacteria Using Immobilized Polyvinyl Alcohol Beads," Journal of Bioscience and Bioengineering, vol. 87, No. 2, (1999), pp. 189-193.

Pashkuleva et al., "Surface Modification of Starch Based Biomaterials Can Simultaneously Enhance Cell Adhesion and Proliferation and Induce Bioactivity," 18th European Conference on Biomaterials, Oct. 1-4, 2003, Stuttgard, Germany, p. T103.

(56) References Cited

OTHER PUBLICATIONS

Quan et al., "Reject Water Treatment by Improvement of Whole Cell Anammox Entrapment Using Polyvinyl Alcohol/Alginate Gel," Biodegradation, Nov. 2011, vol. 22, Issue 6, pp. 1155-1167.
Renner et al., "Physicochemical Regulation of Biofilm Formation," MRS Bulletin, vol. 36, May 2011, pp. 1-9.
Rooke et al., "Novel Photosynthetic CO2 Bioconvertor Based on Green Algae Entrapped in Low-Sodium Silica Gels," J. Mater. Chem., (2011), vol. 21, pp. 951-959.
Sousa et al., "Phenotypic Switching: An Opportunity to Bacteria Thrive," Science against microbial pathogens: communicating current research and technological advances, A. Mendez-Vilas (Ed.), FORMATEX 2011, pp. 252-262.
Stevens et al., "Exploring and Engineering the Cell Surface Interface," Science, vol. 310, Nov. 18, 2005, pp. 1135-1138.
Stolpovsky et al., "Incorporating Dormancy in Dynamic Microbial Community Models," Ecological Modeling 222 (2011) pp. 3092-3102.
Sun et al., "Optimization of Entrapping Conditions of Nitrigying Bacteria and Selection of Entrapping Agent," 2nd International Conference on Environmental Science and Technology IPCBEE, vol. 6. (2011), pp. V2-414-V2-417.
Tiraferri et al., "Hydrophilic Thin-Film Composite Forward Osmosis Membranes Functionalized with Surface-Tailored Nanoparticles," ACS Appl. Materials and Interfaces (2012) vol. 4, pp. 5044-5053.
Tuson et al., "Bacteria-Surface Interactions," The Royal Society of Chemistry (2013), 13 pages.
Voloshin et al., "The Role of Intercellular Contacts in the Initiation of Growth and in the Development of a Transiently Nonculturable State by Cultures of Rhodococcus rhodochrous Grown in Poor Media," Microbiology, vol. 74, No. 4, (2005) pp. 420-427.
Wong et al., "All together now: Integrating Biofilm Research Across Disciplines," MRS Bulletin, vol. 36, May 2011, pp. 339-342.
Solomon; "America's Water and Wastewater Crisis: The Role of Private Enterprise"; 2011; pp. 77-78 and 99; Transaction Publishers, Rutgers; Piscataway, New Jersey.
Contents of website, www.microvi.com, dated Aug. 26, 2009, accessed Nov. 24, 2014.
Shirazi, F. R., et al., "Advanced Microencapsulation for Complete Destruction of MTBE in Groundwater," 9 pages.
Bluestein, A., "Blue is the New Green," Inc., Oct. 2008, p. 128.
Javier, M., "Microvi Focuses on Zero Waste with Biological Water Treatment," Cleantech Group LLC News, Mar. 8, 2010, 2 pages.
Casey, T., Cleantechnica on Mar. 16, 2010 (http://cleantechnica.com/2010/03/16/billions-of-tiny-bugs-have-green-jobs-cleaning-up-polluted-sites/), 6 pages.
"Billions of Tiny Bugs Have Green Jobs Cleaning Up Polluted Sites," Mar. 20, 2010, posting by the Adani Institute of Infrastructure Management (aiim.wordpress.com/tag/microvi-biotech/), 2 pages.
Wesoff, E., "Microvi Eliminates Toxins from Water with No Waste," Greentechmedia, May 14, 2010, 2 pages.
Giles. "Sizing up next-generation municipal wastewater treatment technologies", Lux Populi, Jan. 27, 2012, (http://luxresearchinc.com/blog/author/brent-giles/).
Slideshare Jan. 15, 2011 (http://www.slideshare.net/venturecenter/water-technologies-15jan11) from Cutting Edge Technologies in the Water Industry.
Contents of website, www.microvibiotech.com, dated Apr. 10, 2006, accessed Sep. 3, 2014.
Contents of website, www.microvibiotech.com, dated Feb. 2, 2008, accessed Sep. 3, 2014.
Contents of website, www.microvibiotech.com, dated Jun. 30, 2012, accessed Sep. 3, 2014.
Yarris, Lynn, "New Synthetic Biology Technique Boosts Microbial Production of Diesel Fuel," Berkeley Lab, Lawrence Berkeley National Laboratory, 4 pages.
Zhang et al., "Nitrate Removal by Thiobacillus Dentrificans Immobilized on Poly(vinyl alcohol) Carriers," Journal of Hazardous Materials (2008), 6 pages.
Zhou et al., "Recent Patents on Immobilized Microorganism Technology and Its Engineering Application in Wastewater Treatment," Recent Patents on Engineering, (2008), vol. 2, pp. 28-35.
Pegasus / Pegazur / Bio-Tube Process, Stowa-Selected Technologies, Jun. 13, 2006, 4 pages.
http://books.google.com/books?id_TheEtoLS8kcC &printsec=frontcover#v=onepage&q=butanol&f=false, "Handbook on Clostridia," 372, 2 pages.
http://kurakay-aqua.com.jp/en/product.pvagel.html, "PVA-Gel Bioreactor," Kuraray Aqua Co., Ltd., 3 pages.

\* cited by examiner

ENHANCED EFFICIENCY ETHANOL AND SUGAR CONVERSION PROCESSES

CROSS-REFERENCE TO RELATED APPLICATIONS

Priority is claimed to U.S. Provisional Patent Applications Nos. 61/689,941, 61/689,944 and 61/689,948, filed Jun. 15, 2012, herein incorporated by reference in their entirety.

STATEMENT REGARDING FEDERALLY SPONSORED RESEARCH OR DEVELOPMENT

None

FIELD OF THE INVENTION

This invention pertains to processes for bioconverting sugars to ethanol with enhanced energy and sugar conversion efficiencies.

BACKGROUND

By 2010, the production capacity of ethanol in the United States has exceeded 12 billion gallons per year, much of which is used as alternative fuel. Most of the production in the United States occurs in dry-mill ethanol plants through fermenting corn as the feedstock. The economic viability of an ethanol plant resides in being able to produce ethanol at low cost to be competitive with other ethanol producers and provide ethanol at a price competitive with gasoline. Accordingly, these ethanol plants are highly energy integrated and have capacities greater than 100 million gallons per year to take advantage of economies of scale.

In conventional ethanol plants the sugar source such as one or more of corn, wheat, sugar beets, oats, barley, sugar cane, sorghum, cassava, rice, and the like is milled and subjected to pretreatment which typically includes an enzymatic hydrolysis to convert starches to sugars. The sugars are then fermented to ethanol using a suitable microorganism such as yeast. The fermentation is generally done in batches with each batch being maintained under fermentation conditions for 2 to 4 days. The duration of the fermentation can be varied. As the batch fermentation progresses, the concentration of sugars declines. The rate of conversion of sugars to ethanol decreases as the sugars become depleted or the ethanol concentration attains a concentration that adversely affects the microorganisms. Thus, the operation of the batch fermentations is typically such that for a given amount of sugars provided to the batch reactor sufficient water is present to assure that when the sought amount of sugars are converted, the concentration of ethanol is below that which is unduly deleterious to the microorganisms.

The fermentation broth which contains in an aqueous medium ethanol and other metabolites, any unconverted sugars, and indigestible solids from the sugar source and the microorganisms and their debris, is passed to a beer still to separate ethanol and provide as a bottom stream a whole stillage containing water, solids and higher boiling components. This whole stillage is separated into a liquid fraction (thin stillage) and a concentrated solids fraction typically called distillers grains. The distillers grains can be used as animal feed, and water is usually recovered from the thin stillage for reuse in the process via an evaporation operation. The concentrated stream from the evaporation operation contains sugars and may be discarded or admixed with the distiller grains. The sugars comprise pentose, i.e., five carbon sugars.

These ethanol plants consume considerable amounts of energy, e.g., for distillation to recover ethanol and to recover water used in the fermentation process for recycling to the process. Numerous proposals exist to improve the economics of ethanol plants. However, the viability of any proposal will need to take into account the effect that any change may have on the highly integrated design and on co-products. Most plants derive significant revenue from co-products which are primarily carbon dioxide, distillers grains which are used as animal feed and corn oil.

The unit operations for an ethanol plant are designed for a given production rate of ethanol. The batch fermenters, as discussed above, have a limited window of operation due to constraints on conversion rates and final ethanol concentration. Thus, any increase in ethanol production rate would result in a greater flow rate of feed to the beer still. The beer still and the available steam are designed for a maximum flow rate. Thus in order to operate within the constraints of an existing ethanol plant, the operator must determine whether the batch fermentation conditions should favor maximizing the rate of production of ethanol per unit time or maximizing the conversion of sugars in the sugar source to ethanol. Where demand for ethanol is high, 3 percent or more, and in some instances up to 7 percent, of the available sugars may be unconverted.

Proposals have been made to "setback" a portion of the thin stillage to avoid the energy costs associated with evaporating water from the thin stillage. However, the ability to setback is limited as components contained in the thin stillage can adversely affect the fermentation. Reaney, et al., in U.S. Published Patent Application 2011/0130586 state that metabolites generated in the saccharification and fermentation tanks end up in the thin stillage and at higher concentration levels can inhibit enzyme activities and microbial metabolism. They disclose removing these metabolites and plant extractives and plant derivatives from the thin stillage.

Dale, in U.S. Patent Application Publication 2009/0227004, proposes metabolizing gums in the whole stillage to facilitate removal of corn oil. The adoption of any such process needs to take into account the equipment to effect required and byproducts of any such fermentation in the process.

Abbas, et al., in U.S. Patent Application Publication 2009/0155414, proposes to enhance ethanol fermentation yields by stopping the fermentation when the broth still contains significant amounts of sugars and recovering sugars from the thin stillage. They state at paragraph 0021:

"Optionally, the nutritional value of the distillers' molasses may be increased by treatment and addition of fiber solubles obtained from the ethanol production process. For example, the corn fiber stream derived from a corn wet mill, or the hull fraction from a corn dry grind process may be subjected to a thermochemical and/or enzymatic treatment to solubilize the fiber. The solubilized fiber will include pentose sugars, including but not limited to D-xylose and L-arabinose and their oligosaccharides."

"The solubilized fiber fraction can be mixed with the high-sugar backset prior to partial evaporation to form the distillers' molasses. This can enhance the quality of the distillers' molasses, because the sugars and oligomers have been known and used for their probiotic properties that enhance the resulting feed."

Balan, et al., in U.S. Published Patent Application 2009/0093027 disclose an integrated process involving the addition of corn stillage to lignocellulosic material such as corn stover, and then converting the lignocellulosic material to ethanol.

Accordingly, a need exists to increase the production rate of an existing ethanol plant without undue capital and operating costs while still obtaining a high conversion rate of sugars to ethanol. Also, a desire exists to provide a fermentation broth to the beer still that contains a higher concentration of ethanol and thereby reduce the amount of steam required for the distillation per unit of ethanol produced.

Another desire of existing ethanol plants is to produce higher value bio-products such as hydrocarbons and other organic products such as propanol, propanediol, butanol, butanediol, lactic acid, and the like without undue capital costs.

SUMMARY OF THE INVENTION

The processes of this invention provide for retrofits of existing ethanol plants and auxiliary modules for new conventional ethanol plants using batch fermentation processes to enhance both production rate to ethanol and conversion of sugar to ethanol or to enable the bioconversion of sugars to other bio-products without undue capital and operating costs. The processes of this invention use an overlay fermentation operation. Accordingly, for a given amount of water, additional ethanol can be produced, and thus the beer still and the energy costs to operate the beer still need not be changed or materially changed. Alternatively, the overlay fermentation can be used to bioconvert sugars to other bio-products. The overlay fermentation can, if desired, be used with carbon dioxide as a co-substrate for bioconversions to organic products using microorganisms capable of such bioconversion, e.g., using the Reverse Krebs Cycle, the Reductive acetyl CoA pathway or the 3-hydroxypropriate semi cycle. An example of the use of carbon dioxide as co-substrate proposed for commercialization is the production of succinic acid.

The overlay fermentation can involve an overlay on one or more of the batch fermentation, thin stillage and beer still of an ethanol plant.

A. Batch Fermentation Overlay

The broad aspects of the batch fermentation overlay pertain to processes for producing ethanol by the fermentation of biomass containing carbohydrate comprising:
(a) contacting a solids-containing feedstock comprising fermentable sugars in an aqueous fermentation medium in a batch fermentor and under fermentation conditions including the presence of a microorganism capable of bioconverting sugars to ethanol, to convert a portion of the sugars to ethanol and provide a fermentation broth comprising ethanol, unconverted sugars, solids and water wherein the concentration of ethanol in the aqueous fermentation medium does not exceed that which is unduly deleterious to the microorganism;
(b) during or after step (a) separating at least a portion of the fermentation broth from step (a) to provide a clear liquor containing ethanol, unconverted sugars and water and a concentrated solids fraction comprising ethanol, unconverted sugars, solids and water;
(c) fractionating by distillation at least a portion of the concentrated solids fraction to provide an ethanol product fraction and a whole stillage bottoms fraction;
(d) contacting at least a portion of the clear liquor with biocatalyst under metabolic conditions to bioconvert at least a portion of the fermentable sugars in the clear liquor to at least one organic product and provide a first product stream comprising said at least one organic product and water, wherein said biocatalyst comprises
 i. a solid structure of hydrated hydrophilic polymer defining an interior structure having a plurality of interconnected major cavities having a smallest dimension of between about 5 and 100 microns and an HEV of at least about 1000 and
 ii. a population of microorganisms capable of converting sugars to at least one organic product substantially irreversibly retained in the interior of the solid structure, said population of microorganisms being in a concentration of at least about 60 grams per liter based upon the volume defined by the exterior of the solid structure when fully hydrated, and
wherein the first product stream has a substantial absence of solids; and
(e) recovering at least one organic product from the first product stream.

In another broad aspect, the processes for batch fermentation overlay comprise:
(a) separating a process stream containing fermentable sugars and solids in an aqueous medium to provide a clear liquor containing fermentable sugars and water and a concentrated solids fraction comprising fermentable sugars, solids and water;
(b) contacting at least a portion of the clear liquor with biocatalyst under conversion conditions to bioconvert at least a portion of the fermentable sugars in the clear liquor to at least one organic product and provide a first product stream comprising said at least one organic product and water, wherein said biocatalyst comprises:
 i. a solid structure of hydrated hydrophilic polymer defining an interior structure having a plurality of interconnected major cavities having a smallest dimension of between about 5 and 100 microns and an HEV of at least about 1000 and
 ii. a population of microorganisms capable of converting sugars to at least one organic product substantially irreversibly retained in the interior of the solid structure, said population of microorganisms being in a concentration of at least about 60 grams per liter based upon the volume defined by the exterior of the solid structure when fully hydrated, and
wherein the first product stream has a substantial absence of solids;
(c) recovering at least one organic product from the first product stream and providing a water-containing lean stream;
(d) combining at least a portion of the lean stream from step (c) with the concentrated solids fraction of step (a) to provide a combined stream comprising solids, fermentable sugars, and water;
(e) subjecting the combined stream of step (d) fermentation conditions sufficient to convert at least a portion of the fermentable sugars to ethanol to provide an ethanol-containing fermentation broth, said fermentation conditions comprising the presence of microorganism capable of bioconverting sugars to ethanol; and
(f) fractionating by distillation at least a portion of the ethanol-containing fermentation broth to provide an ethanol product fraction and a whole stillage containing water and solids.

B. Thin Stillage Overlay

The broad aspects of the thin stillage overlay pertain to processes for producing ethanol by the fermentation of biomass containing carbohydrate comprising:

a. hydrolyzing an admixture of water, enzyme and biomass under hydrolyzing conditions sufficient to convert carbohydrate by enzymatic hydroysis and provide a hydrolysate containing pentose and hexose;
b. subjecting at least a portion of the hydrolysate to fermentation conditions sufficient to convert at least a portion of the hexose to ethanol to provide an ethanol-containing fermentation broth, said fermentation conditions comprising the presence of microorganism capable of converting hexose to ethanol, and said ethanol-containing fermentation broth containing solids;
c. fractionating by distillation at least a portion of the ethanol-containing fermentation broth to provide an ethanol product fraction and a whole stillage containing water, solids and unfermented sugars comprising pentose;
d. separating at least a portion of the whole stillage to provide a thin stillage containing pentose and having an essential absence of solids and to provide a solids-containing fraction, often the fermentable sugars in the thin stillage are in a concentration of between about 10 and 50, say 3 and 40, grams per liter;
e. contacting under fermentation conditions in a fermentation zone at least a portion of the thin stillage with biocatalyst said biocatalyst comprising:
   i. a solid structure of hydrated hydrophilic polymer defining an interior structure having a plurality of interconnected major cavities having a smallest dimension of between about 5 and 100 microns and an HEV of at least about 1000 and
   ii. a population of microorganisms capable of converting pentose to ethanol substantially irreversibly retained in the interior of the solid structure, said population of microorganisms being in a concentration of at least about 60 grams per liter based upon the volume defined by the exterior of the solid structure when fully hydrated,
to provide a treated thin stillage having a reduced pentose content and substantially no solids;
f. withdrawing the treated thin stillage from the fermentation zone while retaining the biocatalyst in the fermentation zone;
g. evaporating water and ethanol from at least a portion of the treated thin stillage to provide a concentrated solubles product and vapor; and
h. passing at least a portion of the evaporated water and ethanol to step (a).

In its broad aspects, the thin stillage overlay provides a number of advantages. For instance, at least a portion of the sugars contained in the thin stillage are converted to ethanol without generating solid waste that must be removed from the thin stillage prior to being sent to the evaporators. Moreover, the evaporation operation of recovers the produced ethanol and enables its recycle to the hydrolyzing step with water recovered from the thin stillage in the evaporation operation. This ethanol is thus recovered in the fractionation of step (c) thereby eliminating the need for any additional ethanol distillation equipment. In a preferred embodiment of this invention, the concentrated solubles are admixed with at least a portion of the solids from step (d).

In an additional embodiment of the thin stillage overlay, the thin stillage contains metabolites and the fermentation of step (e) bioconverts at least a portion of the metabolites to one or more of bioproducts that not as adverse to the fermentation of step (b) than the metabolites, thereby enhancing the ability to setback thin stillage without the need for processing in the evaporation operation of step (g) thereby reducing energy costs. In this aspect of the invention, an aliquot portion of the treated thin stillage from step (e) is thus passed to step (a). The bioconversion of the metabolites may be anabolic or catabolic. In another preferred embodiment of the invention, the evaporating of step (g) is conducted in at least two effects, and vapor from at least the first effect is passed to the fractionation of step (c), and vapor from at least the last effect is passed to step (a). In this manner, essentially no ethanol will be contained in the water recycled to the hydrolysis of step (a) and the fermentation of step (b) can be essentially reduced.

In another embodiment of the thin stillage overlay, the fermentation of step (b) is conducted to enhance the rate of production of ethanol but at a lower conversion of sugars, and the fermentation of the thin stillage of step (e) is used to achieve desired conversion of the sugars and microorganisms capable of converting pentanose and hexanose to ethanol are contained in one or more biocatalysts. In this mode of operation, the conversion of hexose to ethanol in step (b) is less than about 97, say, less than about 95, percent. The rate of conversion of sugars to ethanol decreases as the concentration of ethanol in a fermentation broth increases and decreases as the concentration of sugars decrease. Thus, an operator has the flexibility to determine in a conventional ethanol plant operation where to operate in the continuum between maximizing ethanol production and maximizing corn sugar conversion. The processes of this invention, by bioconverting sugars in the thin stillage, enable the operator to obtain both high rates of production of ethanol and high conversion efficiencies.

In yet a further preferred embodiment of the thin stillage overlay, the fermentation of step (e) is conducted on a continuous basis. Due to the high solids content in the feed derived from either the wet mill or dry mill processes, the hydrolyzate is typically fermented in a batch mode with free yeasts to facilitate contact between the yeasts and sugars. Accordingly, the fermentation broth taken from the batch reactors contains yeasts and solid wastes from the yeasts. Another reason for the batch operation is that new charges of yeasts can be used for every fermentation reactor cycle and thereby avoid any phage or autogenetic change that might occur over long durations of use. The processes of this invention provide to the bioconversion of step (e) a stream relatively free of solids that has been subjected to fractionation conditions which often denature the stream. Additionally, the ability to increase cell density using the biocatalysts over that achievable in batch reactors using a free suspension of microorganisms, is advantageous for obtaining attractive conversions of the low concentrations of sugars in the thin stillage.

C. Beer Still Overlay

In its broad aspects, the beer still overlay processes comprise:

(a) passing an aqueous, ethanol-containing fermentation broth, which broth also contains solids, to a distillation zone;
(b) fractionating by distillation said fermentation broth in said distillation zone to provide a lower-boiling, ethanol-rich stream and a higher boiling, aqueous stream which also contains solids;

(c) withdrawing from said distillation zone a side stream comprising ethanol and water and having a substantial absence of solids;
(d) subjecting the withdrawn side stream to fermentation conditions in at least one fermentation zone including the presence of at least one biocatalyst capable of bioconverting ethanol or ethanol metabolite to another organic product to provide a bioconversion effluent comprising the another organic product, ethanol, and water, and preferably having a substantial absence of solids, wherein:
(i) said biocatalyst comprises:
A. a solid structure of hydrated hydrophilic polymer defining an interior structure having a plurality of interconnected major cavities having a smallest dimension of between about 5 and 100 microns and an HEV of at least about 1000 and
B. a population of microorganisms capable of converting ethanol or ethanol metabolite substantially irreversibly retained in the interior of the solid structure, said population of microorganisms being in a concentration of at least about 60 grams per liter based upon the volume defined by the exterior of the solid structure when fully hydrated,
(ii) said biocatalyst is retained in said at least one fermentation zone,
(ii) said withdrawn side stream is passed continuously through said at least one fermentation zone and said bioconversion effluent is withdrawn continuously from said at least one fermentation zone; and
(iii) said withdrawn side stream has an ethanol concentration below that which adversely affects the biocatalyst in the porous matrices, preferably said side stream having an ethanol concentration of less than about 25 mass percent;
(e) recovering at least a portion of the another organic product from said bioconversion effluent; and
(f) passing at least a portion of the ethanol and water in the bioconversion effluent to the distillation zone.

In one embodiment of the processes of the invention, at least an aliquot portion of the bioconversion effluent is passed to the distillation zone and the fractionating of step (b) provides another organic compound-rich stream. In different embodiment, the bioconversion effluent is passed to at least one recovery zone to provide a higher organic compound-rich stream and at least one aqueous stream containing ethanol and water, and at least a portion of the aqueous stream is passed to the distillation zone.

In another embodiment of the invention an additional substrate is added to the at least one fermentation zone. The substrate may be a co-substrate such as carbon dioxide to bioconvert ethanol to succinic acid.

In yet another embodiment of the invention, the fermentation zone contains at least two different biocatalysts, at least one of which is adapted to bioconvert ethanol to at least one ethanol fermentation product and at least one of which is adapted to bioconvert at least one ethanol metabolite to another organic product. Often the ethanol metabolite comprises one or more of acetaldehyde, acetic acid or salt thereof, pyruvic acid or salt thereof, acetyladenylate, and acetyl CoA.

DETAILED DESCRIPTION

Figure 1:
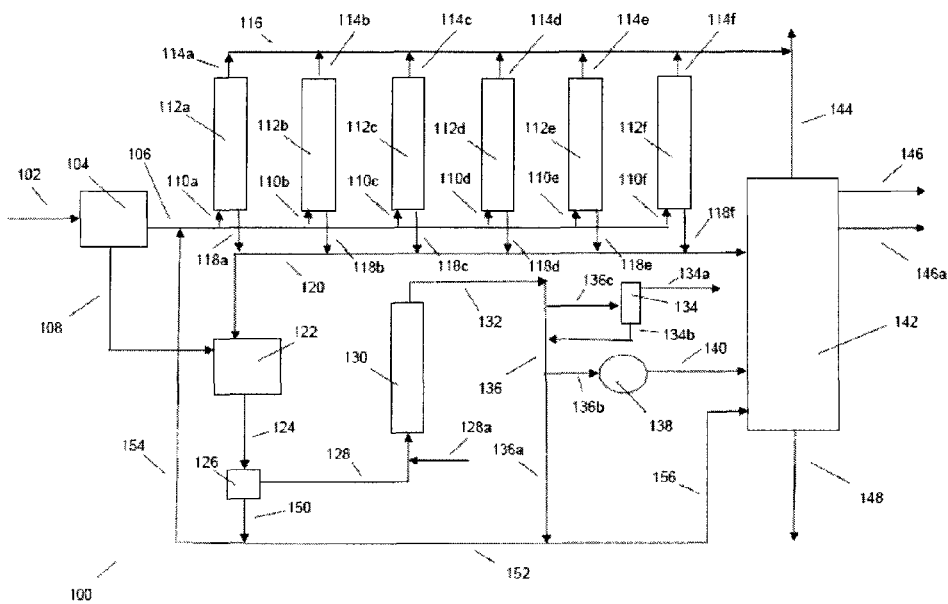
FIG. 1 is a schematic depiction of an ethanol plant capable of being operated in accordance with a batch fermentation overlay process of this invention.

All patents, published patent applications and articles referenced in this detailed description are hereby incorporated by reference in their entireties.

Definitions

As used herein, the following terms have the meanings set forth below unless otherwise stated or clear from the context of their use.

The use of the terms "a" and "an" is intended to include one or more of the element described. Lists of exemplary elements are intended to include combinations of one or more of the element described. The term "may" as used herein means that the use of the element is optional and is not intended to provide any implication regarding operability.

Adhering to the solid structure of the biocatalyst means that the microorganisms are located in cavities in the interior of the biocatalyst and are substantially irreversibly retained therein although extraordinary conditions and treatments (i.e., not normal bioconversion conditions for bioconversion using the microorganisms) might be able in some instances to cause the microorganism to exit the biocatalyst. Adhering includes surface attachment to the polymer forming the walls of the porous matrix as well as where the retained microorganisms are proximate to a polymeric surface, e.g., within about 10 or 20 microns, but not directly contacting the surface. Adhering thus includes physical and electrostatic adherence. In some instances, the polymer used to make the biocatalyst may become embedded in the extracellular polymeric substance around a cell or even in or on the cell wall of the microorganism.

Bioconversion activity is the rate of consumption of substrate per hour per gram of microorganism. Where an increase or decrease in bioconversion activity is referenced herein, such increase or decrease is ascertained under similar bioconversion conditions including concentration of substrate and product in the aqueous medium. Bioconversion activity to bioproduct is the rate of production of the bioproduct per hour per gram of microorganism.

Biofilm means an aggregate of microorganisms embedded within an extracellular polymeric substance (EPS) generally composed of polysaccharides, and may contain other components such as one or more of proteins, extracellular DNA and the polymer used to make the biocatalyst. The thickness of a biofilm is determined by the size of the aggregate contained within a continuous EPS structure, but a continuous EPS structure does not include fibrils that may extend between separated biofilms. In some instances, the biofilm extends in a random, three dimensional manner, and the thickness is determined as the maximum, straight line distance between the distal ends. A thin biofilm is a biofilm which does not exceed about 10 microns in any given direction.

Bioproduct means a product of a bioconversion which may be an anabolic product or a catabolic product and includes, but is not limited to, primary and secondary metabolites.

A state of essential stasis means that a microorganism population has undergone a substantial cessation of metabolic bioconversion activity but can be revived. The existence of an essential stasis condition can be ascertained by measuring bioconversion activity. The essential stasis condition may be aerobic, anoxic or anaerobic which may or may not be the same as that of normal operating conditions for the microorganism. Where stasis is sought, the temperature is typically in the range of about 0° C. to 25° C., say, 4° C. to 15° C. which may be different from the temperatures used at normal operating conditions.

An exo-network is a community of spaced-apart microorganisms that can be in the form of individual cells or biofilms that are interconnected by extracellular polymeric substance in the form of strands. The spacing between the microorganisms or biofilms in the exo-network is sufficient to enable the passage of nutrients and substrates there between and is often at least about 0.25, say, at least about 0.5, micron and may be as large as 5 or 10 microns or more.

Exterior skin is an exterior layer of polymer on the biocatalyst that is less open than the major channels in the interior structure of the biocatalyst. A biocatalyst may or may not have a skin. Where a skin is present, it may or may not have surface pores. Where no surface pores are present, fluids diffuse through the skin. Where pores are present, they often have an average diameter of between about 1 and 10 microns.

Fully hydrated means that a biocatalyst is immersed in water at 25° C. until no further expansion of the superficial volume of the biocatalyst is perceived.

The "Hydration Expansion Volume" (HEV) for a biocatalyst is determined by hydrating the biocatalyst in water at 25° C. until the volume of the biocatalyst has stabilized and measuring the superficial volume of the biocatalyst ($V_w$), removing the biocatalyst from water and removing excess water from the exterior, but without drying, and immersing the biocatalyst in ethanol at 25° C. for a time sufficient that the volume of the biocatalyst has stabilized and then measuring the superficial volume of the biocatalyst ($V_s$).

The HEV in volume percent is calculated as the amount of $[V_w/V_s] \times 100\%$.

To assure dehydration with the ethanol, either a large volume ratio of ethanol to biocatalyst is used or successive immersions of the biocatalyst in fresh ethanol are used. The ethanol is initially dehydrated ethanol.

Irreversibly retained and substantially irreversibly retained mean that the microorganisms are adhering to polymeric structures defining open, porous cavities. Irreversibly retained microorganisms do not include microorganisms located on the exterior surface of a biocatalyst. A microorganisms is irreversibly retained even if the biocatalyst has exterior pores of sufficient size to permit egress of the microorganisms.

Highly hydrophilic polymers are polymers to which water is attracted, i.e., are hydroscopic. Often the polymers exhibit, when cast as a film, a water contact angle of less than about 60°, and sometimes less than about 45°, and in some instances less than about 10°, as measured by the sessile drop method using a 5 microliter drop of pure distilled water.

Highly hydrated means that the volume of the biocatalyst (excluding the volume of the microorganisms) is at least about 90 percent water.

A matrix is an open, porous, polymeric structure and is an article of manufacture having an interconnected plurality of channels or cavities (herein "major cavities") defined by polymeric structures, said cavities being between about 5 and 100 microns in the smallest dimension (excluding any microorganisms contained therein), wherein fluid can enter and exit the major cavities from and to the exterior of the matrix. The porous matrix may contain larger and smaller channels or cavities than the major cavities, and may contain channels and cavities not open to the exterior of the matrix. The major cavities, that is, open, interconnected regions of between about 5 or 10 to 70 or 100 microns in the smallest dimension (excluding any microorganism contained therein) have nominal major dimensions of less than about 300, preferably less than about 200, microns, and sometimes a smallest dimension of at least about 10 microns. The term open, porous thus refers to the existence of channels or cavities that are interconnected by openings therebetween.

Metabolic conditions include conditions of temperature, pressure, oxygenation, pH, and nutrients (including micronutrients) and additives required or desired for the microorganisms in the biocatalyst. Nutrients and additives include growth promoters, buffers, antibiotics, vitamins, minerals, nitrogen sources, and sulfur sources and carbon sources where not otherwise provided.

An organic compound is a compound containing carbon atoms bonded to at least one of hydrogen, oxygen, nitrogen, phosphorus, and sulfur atoms other than carbon dioxide, carbon monoxide, carbides, carbonates, cyanides, cyanates, and thiocyanates. Examples of organic compounds include, but are not limited to, one or more of aliphatic compounds and aromatic compounds including but not limited to hydrocarbons of up to 44 or 50 carbons, and hydrocarbons substituted with one or more of hydroxyl, acyl, carboxyl, amine, amide, halo, nitro, sulfonyl, and phosphino moieties, and hydrocarbons containing one or more hetero atoms including but not limited to, nitrogen, sulfur, oxygen, and phosphorus atoms. Examples of organic products as end products from metabolic processes are those listed in United States published patent application no. 2010/0279354 A1, especially as set forth in paragraphs 0129 through 0149. See also, United States published patent application no. 2011/0165639 A1. Other bioproducts include p-toluate, terephthalate, terephthalic acid, aniline, putrescine, cyclohexanone, adipate, hexamethylenediamine (HMDA), 6-aminocaproic acid, malate, acrylate, apidipic acid, methacrylic acid, 3-hydroxypropionic acid (3HP), succinate, butadiene, propylene, caprolactam, fatty alcohols, fatty acids, glycerates, acrylic acid, acrylate esters, methacrylic acid, methacrylic acids, fucoidan, muconate, iodine, chlorophyll, carotenoid, calcium, magnesium, iron, sodium, potassium, and phosphate. The bioproduct may be a chemical that provides a biological activity with respect to a plant or animal or human. The biological activity can be one or more of a number of different activities such as antiviral, antibiotic, depressant, stimulant, growth promoters, hormone, insulin, reproductive, attractant, repellant, biocide, and the like. Examples of antibiotics include, but are not limited to, aminoglycosides (e.g., amikacin, gentamicin, kanamycin, neomycin, netilmicin, tobramycin, paromomycin); ansamycins (e.g., geldanamycin, herbimycin); carbacephem (loracarbef); carbapenems (e.g., ertapenem, doripenem, imipenem/cilastatin, meropenem); cephalosporins (first generation, e.g., cefadroxil, cefazolin, cefalotin, cefalexin); cephalosporins (second generation, e.g., cefaclor, cefamandole, cefoxitin, cefprozil, cefuroxime); cephalosporins (third generation, e.g., cefixime, cefdinir, cefditoren, cefoperazone, cefotaxime, cefpodoxime, ceftazidime, ceftibuten, ceftizoxime, ceftriaxone); cephalosporins (fourth generation, e.g., cefepime); cephalosporins (fifth generation, e.g., ceftobiprole); glycopeptides (e.g., teicoplanin, vancomycin, telavancin); lincosamides (e.g., clindamycin, lincomycin); macrolides (e.g., azithromycin, clarithromycin, dirithromycin, erythromycin, roxithromycin, troleandomycin, telithromycin spectinomycin); monobactams (e.g., aztreonam); nitrofurans (e.g., furazolidone, nitrofurantoin); penicillins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin); penicillin combinations (e.g., amoxicillin/clavulanate, ampicillin/sulbactam, piperacillin/tazobactam, ticarcillin/clavulanate); polypeptides (e.g., bacitracin, colistin, polymyxin B); quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin); sulfonamides (e.g., mafenide; sulfonamidochrysoidine, sulfacetamide, sulfadiazine, silver sulfadiazine, sulfamethizole, sulfamethoxazole, sulfanilimide, sulfasalazine, sulfisoxazole, trimethoprim, trimethoprim-Sulfamethoxazole (Co-trimoxazole) (TMP-SMX); tetracyclines (e.g., demeclocycline, doxycycline, minocycline, oxytetracycline, tetracycline); drugs against mycobacteria (e.g., clofazimine, dapsone, capreomycin, cycloserine, ethambutol, ethionamide, isoniazid, pyrazinamide, rifampin, rifabutin, rifapentine, streptomycin) and others (e.g., arsphenamine, chloramphenicol, fosfomycin, fusidic acid, linezolid, metronidazole, mupirocin, platensimycin, luinupristin/dalfopristin, rifaximin, thiamphenicol, tinidazole).

Oxygenated organic product means a product containing one or more oxygenated organic compounds having 2 to 100, and frequently 2 to 50, carbons and at least one moiety selected from the group consisting of hydroxyl, carbonyl, ether and carboxyl. Most preferred oxygenated organic product includes methanol, ethanol, acetic acid, n-propanol, i-propanol, propionic acid, n-butanol, i-butanol, butyric acid, acetone, and methyl ethyl ketone.

Permeable means that a component can enter or exit the major cavities from or to the exterior of the biocatalyst.

A phenotypic change or alternation or phenotypic shift is a change in a microorganism's traits or characteristics from environmental factors and is thus different from a change in the genetic make-up of the microorganism.

Population of microorganisms refers to the number of microorganisms in a given volume and include substantially pure cultures and mixed cultures.

Quiescent means that the aqueous medium in a biocatalyst is still; however, flows of nutrients and substrates and bioproducts can occur through the aqueous medium via diffusion and capillary flow.

Retained solids means that solids are retained in the interior of the biocatalyst. The solids may be retained by any suitable mechanism including, but not limited to, restrained by not being able to pass through pores in the skin of a biocatalyst, by being captured in a biofilm or a polysaccharide structure formed by microorganisms, by being retained in the polymeric structure of the biocatalyst, or by being sterically entangled within the structure of the biocatalyst or the microorganisms.

Smallest dimension means the maximum dimension of the shortest of the maximum dimensions defining the length, width and height of a major cavity. Usually a preponderance of the major cavities in a matrix are substantially width and height symmetrical. Hence the smallest dimension can be approximated by the maximum width of a cavity observed in a two dimensional cross section, e.g., by optical or electronic microscopy.

A solubilized precursor for the polymer is a monomer or prepolymer or the polymer itself that is dissolved or dispersed such that solids cannot be seen by the naked eye and is stable. For instance, a solid can be highly hydrated and be suspended in an aqueous medium even though the solid is not dissolved.

A stable population of microorganisms means that the population of microorganisms does not decrease by more than 50 percent nor increase by more than 400 percent.

Sugar means carbohydrates having 5 to 12 carbon atoms and includes, but is not limited to, D-glyceraldehyde, L-glyceraldehyde, D-erythrose, L-erythrose, D-threose, L-threose, D-ribose, L-ribose, D-lyxose, L-lyxose, D-allose, L-allose, D-altrose, L-altrose 2-keto-3-deoxy D-gluconate (KDG), D-mannitol, guluronate, mannuronate, mannitol, lyxose, xylitol, D-glucose, L-glucose, D-mannose, L-mannose, D-gluose, L-gluose, D-idose, L-idose, D-galactose, L-galactose, D-xylose, L-xylose, D-arabinose, L-arabinose, D-talose, L-talose, glucuronate, galacturonate, rhamnose, fructooligosaccharide (FOS), galactooligosaccharide (GOS), inulin, mannan oligosaccharide (MOS), oligoalginate, mannuronate, guluronate, alpha-keto acid, or 4-deoxy-L-erythro-hexoselulose uronate (DEHU).

Typical Separation Techniques for chemical products include phase separation for gaseous chemical products, the use of a still, a distillation column, liquid/liquid phase separation, gas stripping, flow-through centrifuge, Karr column for liquid-liquid extraction, mixer-settler, or expanded bed adsorption. Separation and purification steps may proceed by any of a number of approaches combining various methodologies, which may include centrifugation, filtration, reduced pressure evaporation, liquid/liquid phase separation, membranes, distillation, and/or other methodologies recited in this patent application. Principles and details of standard separation and purification steps are known in the art, for example in "Bioseparations Science and Engineering," Roger G. Harrison et al., Oxford University Press (2003), and Membrane Separations in the Recovery of Biofuels and Biochemicals—An Update Review, Stephen A. Leeper, pp. 99-194, in Separation and Purification Technology, Norman N. Li and Joseph M. Calo, Eds., Marcel Dekker (1992).

The wet weight or wet mass of cells is the mass of cells from which free water has been removed, i.e., are at the point of incipient wetness. All references to mass of cells is calculated on the basis of the wet mass of the cells.

References to organic acids herein shall be deemed to include corresponding salts and esters.

References to matrix dimensions and volumes herein are of fully hydrated matrices unless otherwise stated or clear from the context.

Reference is made to the drawings for purposes of facilitating the broad aspects of the processes of this invention. The drawings, however, is not in limitation of the invention. The drawings omit minor equipment such as pumps, compressors, valves, instruments and other devices the placement of which and operation thereof are well known to those practiced in chemical engineering. The drawings also all omit ancillary unit operations.

FIG. 1—Batch Fermentation Overlay

Ethanol plant 100 is supplied with a sugar-containing biomass from either wet milling or dry milling via line 102. Any sugar-containing biomass may be used such as corn, wheat, sugar beets, oats, barley, sugar cane, sorghum, cassava, rice, and the like, and mixtures of two or more. For purposes of illustration only, and not in limitation, reference will be made to corn being the sugar-containing biomass.

The corn may be prefractionated to remove one or more components such as oils, proteins, and the like. The milled corn is provided in the form of a slurry, or mash, in water and is passed to liquefaction reactor 104 which contains enzymes such as α-amylase and glucoamylase to convert starches to sugars, i.e., saccharification. The saccharification is often conducted at elevated temperatures, e.g., in the range of 30° C. to 70° C. The saccharification may be preceded by a cooking of the mash at temperatures from about 50° C. up to 150° C. or more to help break down grain structure.

The depicted apparatus can be operated in different modes within the scope of one or more aspects of the processes of this invention. Various modes of operation include:

Ethanol Mono-product Mode (EM Mode) wherein the product of the fermentation of the clear liquor is ethanol; and Dual Product Mode (DP Mode) where the product of the fermentation of the clear liquor is an organic product other than ethanol.

In either the EM Mode or the DP Mode, the clear liquor for the fermentation may be obtained from one or both of the mash and the fermentation broth from fermentation of the mash.

As shown, the mash is capable of being passed directly to an ethanol fermentation via line 106 or being passed via line 108 to a separation operation to provide a clear liquor and a concentrated solids fraction. In practice, all, a portion, or none of the mash is passed into line 106 and all, a portion or none of the mash is passed into line 108. In general, in the EM Mode, at least about 70, preferably at least about 90, and frequently essentially all the mash is passed via line 106. In the DP Mode, the portion of the mash passing via line 108 to the solids separation operation often depends upon the relative production of the organic product to ethanol sought for the plant. With higher relative production of organic product to ethanol, the greater the fraction of the mash transported from liquefaction reactor 104 via line 108 as compared to line 106.

Taking one mode of operation for purposes of illustration, essentially all the mash is passed via line 108 to surge tank 122. Surge tank 122 is optional and serves to provide a reservoir from which a constant flow can be obtained. The mash in surge tank 122 is passed via line 124 to solids separator 126 to provide a clear liquor and a concentrated solids fraction. Solids separator 126 may be any suitable apparatus of series of apparatus to provide the clear liquor. Solids separating apparatus include filters, decanters and settling ponds, and centrifuges. Preferably the clear liquor is substantially free of solids, and any solids present should be sufficiently minute that they pose no untoward problem during fermentation using biocatalysts. Often, the separation is sufficiently efficient that the clear liquor contains less than about 1, preferably less than about 0.1, mass percent solids having a maximum particle dimension greater than about 0.1 micron. The portion of the water passing to the clear liquor can vary over a wide range. The amount of water retained in the concentrated solid fraction should, however, be sufficient to enable the fraction to be transported. Where water is added to the concentrated solids fraction prior to subsequent processing, the portion of the water removed during the separation operation may be greater. Often, between about 10 and 90, say, 20 to 80, and sometimes between about 40 and 75, volume percent of the water are removed in solids separator 126. The solids content of the concentrated solids fraction is generally in the range of 20 to 80, say, 25 to 60, mass percent. The clear liquor is withdrawn from solids separator 126 via line 128 and its processing will be described later.

As shown, the concentrated solids fraction is withdrawn from solids separator 126 via line 150 and passed to header 152. Header 152 can provide a number of operations which will be described herein. One operation is to direct the concentrated solids fraction via line 154 to be combined with mash (if any) in line 106. Line 106 is a header supplying via lines 110 (a, b, c, d, e, and f) each of a plurality of batch reactors 112 (a, b, c, d, e, and f) with feed for the fermentation to ethanol. Six parallel fermentation reactors 112 (a, b, c, d, e, and f) are, for purposes of illustration, operated and cycled in time sequence to level out the production rate. Each of fermentation reactors 112 (a, b, c, d, e, and f) is provided with yeast such as strains of the *Saccharomyces* spp., such as *Saccharomyces* cerevisia, for the conversion of sugars to ethanol. In some instances, the saccharification and fermentation are conducted in the same vessel. The fermentation is typically conducted at a temperature in the range of about 25° C. to 35° C. Usually the residence time in a reactor between about 24 and 96 hours with the reactors started up in sequence to provide an available supply of fermentation broth for continuous recovery of ethanol. Nutrients and adjuvants may be added to the fermentation broth. During the fermentation, carbon dioxide is generated and can be withdrawn from each reactor 112 (a, b, c, d, e, and f) via the respective lines 114 (a, b, c, d, e, and f) and sent to header 116.

At the conclusion of the fermentation cycle for a given reactor 112 (a, b, c, d, e, and f), the fermentation broth, which comprises ethanol and solids in an aqueous medium, is withdrawn via the respective line 118 (a, b, c, d, e, and f) and passed to header 120. Header 120 is adapted to direct all, a portion or none of the fermentation broth to beer still 142 and to direct all, a portion or none of the fermentation broth to surge tank 122. The selection of mode of operation will, in part, depend upon whether the EM Mode or DP Mode is being employed and the objective of the operator in balancing between the fermentation in reactors 112 (a, b, c, d, e, and f) and the fermentation of the clear liquor in bioreactor 130 as described below. In the EM Mode, the election is often based upon the combination of sought rate of production of ethanol and conversion of sugars in the mash. Thus, at lower ethanol production rates, higher conversions of sugars contained in the mash to ethanol may be obtained through using longer fermentation times in reactors 112 (a, b, c, d, e, and f), and less advantage may be obtained by the use of the clear liquor fermentation. But in most instances, in the EM Mode, virtually all the fermentation broth is passed to surge tank 122. In the DP Mode, the operator may elect not to pass the fermentation broth to surge tank 122 if the presence of ethanol in the clear liquor may not be desired for the fermentation to produce the other chemical product. In such case, virtually all the fermentation broth from reactors 112 (a, b, c, d, e, and f) is passed via header 120 to beer still 142. Note that the schematic representation in FIG. 1 shows the fermentation broth being introduced at an elevated portion of beer still 142. In practice, the fermentation broth would be introduced at the bottom of beer still 142. The operation of beer still 142 will be described later.

Returning to line 128, the clear liquor is passed to bioreactor 130. Bioreactor 130 is maintained under metabolic conditions. In some instances, the biocatalysts can facilitate maintaining high cell densities in the aqueous medium and thus facilitate control of the bioconversion system. The biocatalysts are described further below.

Bioreactor 130 contains one or more biocatalysts. The porous polymeric matrices are physically maintained bioreactor 130. Bioreactor 130 may be of any suitable design. Exemplary designs include, but are not limited to, bubble column reactors, stirred reactors, packed bed reactors, trickle bed reactors, fluidized bed reactors, plug flow (tubular) reactors, and membrane (biofilm) reactors.

The biocatalyst may be freely mobile in the fermentation broth or fixed, e.g., to a structure in the reactor vessel, or may itself provide a fixed structure. Where two or more biocatalysts are used, the biocatalysts matrices may be freely mobile, at least one mobile and at least one other fixed, or all may be fixed. Where mobile, the biocatalysts are retained in bioreactor 130 by any suitable means, including, but not limited to, screens, draft tubes, and looped reactors. More than one reactor vessel may be used. For instance, reactor vessels may be in parallel or in sequential flow series.

In addition or alternatively bioreactor 130 may contain biocatalyst effective for the conversion of sugars to another chemical product. The biocatalyst contains microorganisms suitable for making the sought organic product such as described in connection with the discussion regarding the biocatalyst. Line 128a is adapted to provide to bioreactor 130 any additional substrate required or desirable for the bioconversion. For instance, if succinic acid is the sought chemical product, line 128a may provide carbon dioxide.

The fermentation is typically conducted as a continuous fermentation as the biocatalyst is retained in bioreactor 130. The fermentation may be on a continuous, semi-continuous or batch mode of operation. Further the relative amounts of each of the biocatalysts can be established to provide the desired conversion to chemical product.

Where bioreactor 130 is used to produce ethanol, often the concentration of ethanol is the product is at least about 15, preferably at least about 18 or 20, and sometimes up to 25 or 30 or more, mass percent. The biocatalyst used in the processes of this invention permit such high concentrations of ethanol in the aqueous medium to be obtained without undue deleterious effects on the biocatalyst.

The fermentation broth exits bioreactor 130 via line 132, and FIG. 1 depicts three options.

In option A, the fermentation broth in line 132 is passed via line 136a to header 152 where it is directed via line 156 to beer still 142. In one embodiment, the fermentation broth in line 136a is admixed with the concentrated solids fraction from solids separator 126 to facilitate providing a more readily flowable stream to beer still 142.

In option B, the fermentation broth in line 132 is passed via line 136b to indirect heat exchanger 138 which heats the fermentation broth to temperatures suitable for effecting fractionation in beer still 142. The heated fermentation broth is then passed via line 140 to beer still 142. As the fermentation broth is substantially free of solids, the heated fermentation broth can be introduced above the bottom of beer still 142. This provides several advantages. First, as the fermentation in bioreactor 130, where converting sugars to ethanol, may provide a fermentation broth with a higher ethanol concentration than the fermentation broth from reactors 112 (a, b, c, d, e and f), the point of feed introduction can match the theoretical plate of the beer still having that concentration of ethanol. This can reduce energy required by the beer still for the recovery of a given amount of ethanol. Second, the water introduced facilitates the rectification operation of the beer still and the liquid downflow admixes with the solids-containing bottoms to provide a more readily flowable aqueous medium.

In each of options A and B beer still 142 is used to recover ethanol. Especially in the EM Mode, bioreactor 130 serves to increase the ethanol concentration in the fermentation broth. In which case, the energy required per unit of ethanol produced in beer still 142 is reduced. Lights, primarily carbon dioxide, are removed from beer still 142 via line 144. Ethanol is removed via line 146 and may be further processed, e.g., to further reduce water content such as by molecular sieve drying. Line 146a is shown for withdrawing heavier organic compounds from beer still 142. These heavier organic compounds may be fusel oils or sought chemical products. A bottoms fraction from beer still 142 is the whole stillage and is removed via line 148. The bottoms fraction contains solids and water and metabolites such as acetic acid, propionic acid, hydroxypropionic acid, butyric acid, succinic acid, and salts thereof; trimethylammonioacetate; glycerylphosphorylcholine; and aldehydes and hydroxyl-containing compounds such as glycerol, isopropanol, butanol, propanediol, phenylethanol, propanal, and 3-hydroxypropanal. In many conventional ethanol plants the whole stillage is separated into a solids fraction, wet distillers grains, which have utility in animal feeds. The supernatant liquid from the separation, the thin stillage, is usually subjected to evaporation to recover water for reuse in the plant and provide a concentrated fraction which can be disposed or added to the distiller grains.

Option C is primarily used where the objective of bioreactor 130 is to make another organic chemical. As shown, the fermentation broth is passed from line 132 via line 136c to recovery unit 134. Methods for recovery of the organic chemical from the fermentation broth may be any suitable unit operation including, but not limited to, Typical Separation Techniques.

Organic product is recovered from recovery unit 134 via line 134a. If desired, the aqueous medium from which the organic product has been removed, can be passed via line 134b to header 152 and sent either to beer still 142 or admixed with the concentrated solids fraction from solids separator 126 and then passed to line 108 for use in the ethanol fermentation.

Figure 2:
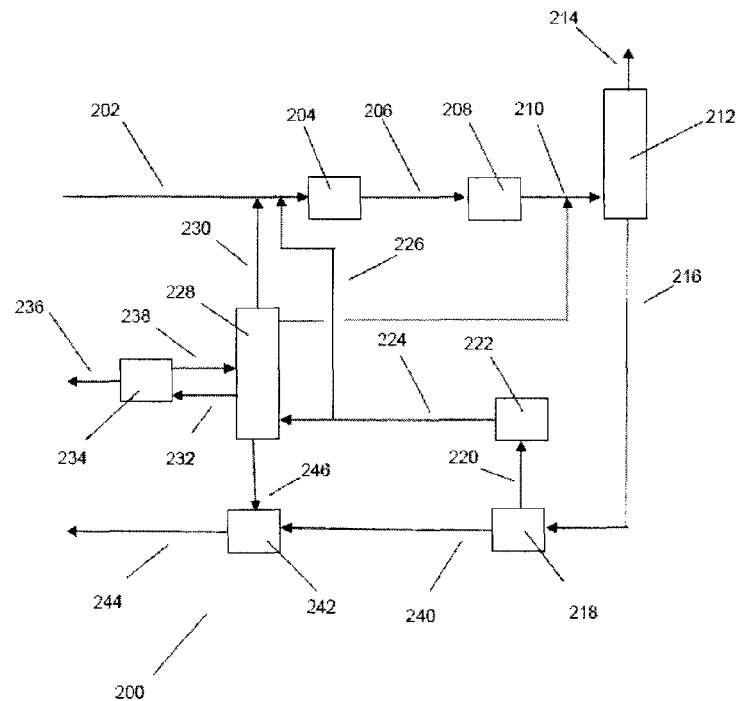
FIG. 2 is a schematic depiction of an ethanol plant capable of being operated in accordance with a this stillage overlay process of this invention.

FIG. 2—Thin Stillage Overlay

Ethanol plant 200 is provided with sugar-containing biomass from either wet milling or dry milling via line 202. Any sugar-containing biomass may be used such as corn, wheat, sugar beets, oats, barley, sugar cane, sorghum, cassava, rice, and the like, and mixtures of two or more. For purposes of illustration only, and not in limitation, reference will be made to corn being the sugar-containing biomass.

The corn may be prefractionated to remove one or more components such as oils, proteins, and the like. The milled corn is provided in the form of a slurry, or mash, in water and is passed to liquefaction reactor 204 which contains enzymes such as α-amylase and glucoamylase to convert starches to sugars, i.e., saccharification as described in connection with FIG. 1. The mash is then passed via line 206 to fermentor 208 where sugars are converted to ethanol. In some instances, the saccharification and fermentation are conducted in the same vessel. The fermentation is typically conducted at a temperature in the range of about 25° C. to 35° C. Usually a plurality of batch reactors operating in parallel is employed with the residence time in a reactor between about 24 and 96 hours with the reactors started up in sequence to provide an available supply of fermentation broth for continuous recovery of ethanol. Nutrients and adjuvants may be added to the fermentation broth.

Fermentation broth from fermentor 208 is supplied to beer still 212 via line 210. Line 210 may include holding tanks to assure a constant supply to beer still 212. Beer still provides an ethanol product stream via line 214. Not shown are other overhead streams such as for carbon dioxide and heavier alcohols. The bottoms from beer still 212 is often referred to as the whole stillage and exits via line 216. The whole stillage is an aqueous stream containing solids derived from the corn and yeast. The whole stillage will also contain non-converted sugars including pentoses such as xylose, mannose, and arabinose and usually some hexoses such s glucose and galactose as the fermentations normally do not consume all hexoses in the feed. The whole stillage will also contain metabolites such as acetic acid, propionic acid, hydroxypropionic acid, butyric acid, succinic acid, and salts thereof; trimethylammonioacetate; glycerylphosphorylcholine; and aldehydes and hydroxyl-containing compounds such as glycerol, isopropanol, butanol, propanediol, phenylethanol, propanal, and 3-hydroxypropanal. The whole stillage may also contain vitamins, minerals, buffers and other adjuvants used in the fermentation of the mash.

The whole stillage is passed by line 216 to centrifuge 218 to separate solids, the distillers grains, from a thin stillage. While a centrifuge is typically used for the separation, other means such as filtration and decanting may find application. The thin stillage from centrifuge 218 is passed via line 220 to bioreactor 222. Bioreactor 222 is maintained under metabolic conditions. Bioreactor 222 contains one or more biocatalysts. Bioreactor 222 is maintained under metabolic conditions.

The biocatalysts are physically maintained bioreactor 222. Bioreactor 222 may be of any suitable design such as described about in connection with bioreactor 130 of FIG. 1.

Often the residence time of the thin stillage in the bioreactor is sufficient to reduce the total sugars (pentose and hexose) to less than about 50, preferably less than about 30, mole percent of the total sugars contained in the thin stillage. The residence time will, however, depend upon the biocatalyst density and fermentation conditions in the bioreactor. As stated above, the bioreactor is preferably operated on a continuous basis. The temperature in the bioreactor should be suitable for the types of biocatalysts contained in the polymeric matrices to provide the sought activity. Often, the biocatalyst is a mesophile or thermophile microorganism and thus the temperature is in the range of about 20° C. to about 60° C., say, about 25° C. to about 40° C.

Bioreactor 222 provides a treated thin stillage that has at least a reduced concentration of total sugars and sometimes a reduced concentration of metabolites. The treated thin stillage exits bioreactor 222 via line 224. Since solids from the fermentation are retained in the polymeric matrices, the treated thin stillage can be fed to evaporator 228 without solids removal operations. Frequently, the composition of the treated thin stillage enables a significant set back of the thin stillage to the feed stream without the need to recover water through evaporation in evaporator 228. For instance, at least about 10, preferably at least about 15, say, about 15 to 50 or more, volume percent of the thin stillage on an aliquot basis can be immediately returned to the feed stream. Line 226 provides for this set back. The set back stream can be added to the feed stream at any convenient point in the process prior to beer still 212. The set back can be used in the wet milling, or used to make the slurry for in a dry milling process. The set back can, in addition or alternatively, be added to one or more of the slurry, or mash, in liquefaction reactor 204 or to fermentor 208.

Returning to line 224 through which treated thin stillage is transported, at least a portion, often at least about 40, say, about 50 to 100, percent of the treated thin stillage is passed to evaporator 228. Evaporator 228 may be a single effect evaporator, but usually 3 or more effects, often 3 to 8 effects, are used. The evaporator may be of any suitable design. Often, the evaporators are thin film evaporators to facilitate transport of the water to the surface of the liquid phase, especially where the viscosity of the liquid phase increases due to concentration of the higher boiling components such as gums and residual sugars. The evaporators are often operated at temperatures between about 70° C. and 120° C., say, 75° C. to 110° C., and under subatmospheric pressure, e.g., from about 10 to 99 kPa.

The evaporator serves to vaporize water and this overhead can be used as process water or discharged from the plant. Typically at least a portion of the water is returned to the process, e.g., to make the slurry for in a dry milling process or, in addition or alternatively, to provide additional water to one or more of the slurry, or mash, in liquefaction reactor 204 or in fermentor 208. As shown, line 230 directs water from evaporator 228 to line 202. As ethanol is contained in the treated thin stillage, ethanol and other lights would also be contained in the overhead.

A preferred embodiment of this invention comprises using a multiple effect evaporator and passing the overhead from at least the first effect to beer still 212. This embodiment is particularly attractive where the fermentation of the corn mash is conducted to achieve higher rates of conversion to ethanol as opposed to greater conversion of sugars to ethanol. Thus the thin stillage contains significant amounts of sugars and the bioconversion in bioreactor 222 provides a high concentration of ethanol in the treated thin stillage, e.g., at least about 1, often about 2 to 12 or more, mass percent ethanol. The first effect of evaporator 228 would thus provide an overhead containing an even higher concentration of ethanol in water, often in the range of about 5 to 25 or more, mass percent. At these higher concentrations, the overhead can be passed via line 230a to beer still 212 for ethanol recovery. Advantageously, the subsequent stages would yield overhead streams containing lesser concentrations of ethanol and therefore would be more suitable for recycling to the corn mash.

Another benefit of the processes of this invention is that the amount of sugars and any other higher boiling components in the thin stillage that are bioconverted in bioreactor 212, are reduced, and hence lesser amounts of concentrate are generated by the evaporator. This can facilitate the recovery of corn oil from the liquor in evaporator 228. Typically corn oil is recovered by passing a stream from one or more of the effects of evaporator via line 232 to centrifuge 234 where the lighter oil is recovered via line 236. The stream can then be returned to evaporator 228 via line 238. The reduction in higher boiling components, including sugars and gums and other plant extracts, due to the bioconversion in bioreactor 222, reduces the amount of bound corn oil thereby enabling its recovery by centrifugation.

The concentrate from evaporator 228 exits via line 246 and may be combined with the distillers grains generated by centrifuge 218. As shown, the distillers grains are passed via line 240 to dryer 242 to provide a dried distillers grains removed via solids removal mechanism 244. The concentrate from evaporator 228 may be admixed with the distillers grains before or during drying or added thereto subsequently. Where a wet distillers grains product is sought, dryer 242 is unnecessary.

Figure 3:
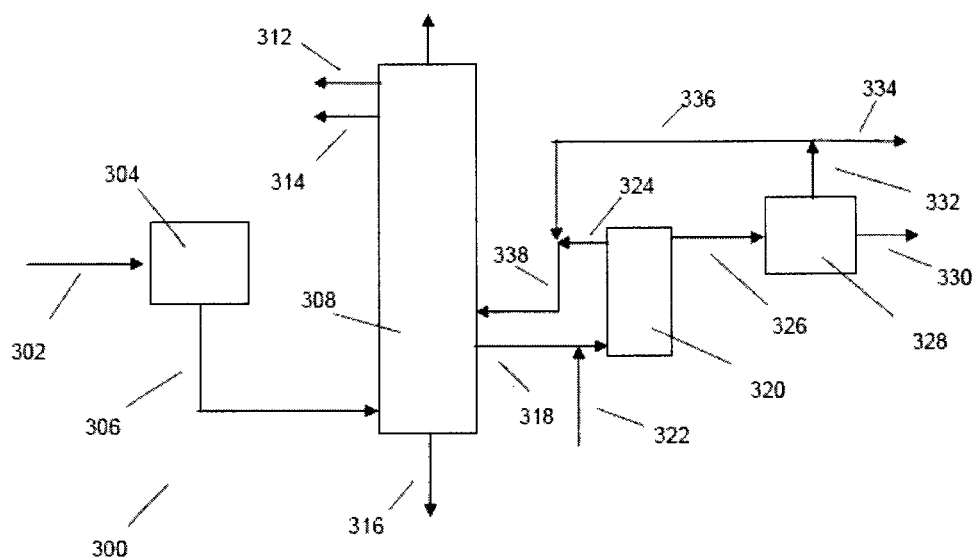
FIG. 3 is a schematic depiction of an ethanol plant capable of being operated in accordance with a beer still overlay process of this invention.

FIG. 3—Beer Still Overlay

A flexible facility for producing ethanol and higher organic compound is generally referenced by the numeral 300. Substrate is supplied via line 302 to ethanol fermentation assembly 304. Ethanol fermentation assembly 304 may be any suitable assembly for bioconverting substrate to ethanol and may comprise one or more unit operations. The fermentation operation may be an aerobic or anaerobic fermentation, and may be continuous, semi-continuous or batch. The substrate may be sugar-containing biomass, cellulose-containing biomass, carbon monoxide-containing gases, which may also contain hydrogen such as syngas, and carbon dioxide. Sugar-containing biomass includes biomass derived from one or more of corn, wheat, sugar beets, oats, barley, sugar cane, sorghum, cassava, rice, and the like. The biomass may be treated prior to fermentation such as by milling, extraction, saccharification, and the like. Carbon monoxide-containing gases may be derived from any suitable source including industrial gases, gasification of biomass, and the like. Carbon dioxide can be obtained from industrial processes, power plants, waste incineration, and the like.

The source of the substrate and type of ethanol fermentation is not critical to the broad aspects of this invention other than ethanol fermentation assembly provides an aqueous ethanol-containing stream (fermentation broth) that also contains solids and that the ethanol concentration is relatively dilute. Typically, the ethanol concentration is in the range of between about 2 and 20, say 3 and 15, mass percent. The solids can comprise solids from the substrate source such as where biomass is used to provide the substrate and the microorganisms used for the fermentation to ethanol and their debris. Often, the fermentation broth contains at least about 1, and sometimes greater than about 4, mass percent solids having a maximum particle dimension greater than about 0.1 micron.

Fermentation broth is passed via line 306 from fermentation assembly 304 to a lower portion of beer still 308. Beer still 308 is adapted to fractionate by distillation the fermentation broth into an ethanol-rich stream and a bottoms stream containing water and solids which has a reduced concentration of ethanol. Beer still 308 may be a single distillation column or two or more columns. Beer still 308 can contain one or more of distillation trays and packing to provide liquid vapor contact.

As shown, lights, which are often carbon dioxide and other normally gaseous components are exhausted from beer still 308. The type of gases and the amounts will depend, in part, on the type of fermentation and its operation. For instance, where biomass is being fermented or carbon dioxide is being bioconverted to ethanol, the gases will contain carbon dioxide. For conversions of syngas, the gases will also contain carbon monoxide and hydrogen.

Ethanol is recovered as an ethanol-rich stream from beer still 308 via line 312. Usually the ethanol-rich stream contains about 95 percent ethanol and is subjected to additional treatment to break the azeotrope and provide substantially anhydrous ethanol which can be denatured for use as an alternative fuel. Line 314 withdraws higher alcohols such as fusel oil, from beer still 308. As described later, one or more side draws such as line 314 may be used to recover higher organic product using the distillation capabilities of beer still 308.

A bottoms stream exits beer still 308 via line 316. The bottoms fraction contains solids and water and higher boiling metabolites of the fermentation to make ethanol. In many conventional ethanol plants the whole stillage is separated into a solids fraction, wet distillers grains, which have utility in animal feeds. The supernatant liquid from the separation, the thin stillage, is usually subjected to evaporation to recover water for reuse in the fermentation to make ethanol and provide a concentrated fraction which can be disposed or added to the distiller grains.

A side draw containing ethanol and water is taken via line 318 from beer still 308 at a point where the liquid medium in beer still 108 is substantially free of solids. Often, the side draw contains less than about 1, preferably less than about 0.1, mass percent solids having a maximum particle dimension greater than about 0.1 micron. Contact with the down-flowing liquid reflux in the beer still 308 facilitates removal of solids from up-flowing vapors. Accordingly considerable flexibility exists in determining the height of the side draw, and thus the ethanol concentration in the liquid phase, from beer still 308. A single point in the distillation process may be used to withdraw the side stream, or alternatively two or more points may be used. For purposes of facilitating description of the drawing, reference will be made to a single side draw point; however, it is within the broad scope of this invention to use two or more side draw points in the distillation operation. The concentration of ethanol in the side draw may approximate that in the fermentation broth passed to beer still 308 or may be at a higher concentration. The sought concentration should not be so great that the side draw adversely affects the biocatalyst used to make the other bioproduct. The biocatalysts exhibit greater tolerance to toxins such as ethanol and ethanol metabolites and to the sought higher organic compounds than do microorganisms that are in free suspension. Higher ethanol concentrations without adversely affecting the biocatalysts, can facilitate the operation of a continuous bioconversion process with high productivities per liter of reactor volume per unit time. Often, the concentration of ethanol in the side draw is at least about 15, mass percent, and is frequently in the range of about 18 to 30, preferably, 18 to 25, mass percent.

The volume of the side draw can vary from none where ethanol is the sought product to virtually 100 percent of the liquid at the point of the side draw depending upon the design of beer still 308 and the capacity of the bioconversion reactor assembly to make the other bioproduct. In some instances, two or more distillation effects may be used and the side draw is taken between the effects. In other instances, the side draw may be from a distillation plate or collection structure within beer still 308.

The side draw is passed via line 318 to bioreactor 320. Bioreactor 320 may be an assembly of one or two or more reactors. Where two or more reactors are used, the reactors may be in parallel or in sequential flow relationship. For the bioconversion to some higher organic products co-substrates may be necessary. For instance, if succinic acid is the desired higher organic product, carbon dioxide would be used as a co-substrate. Co-substrates, if necessary, are provided via line 322.

Bioreactor 320 contains one or more biocatalysts for the bioconversion to higher organic product. The biocatalyst is physically maintained bioreactor 120. Bioreactor 320 may be of any suitable design such as described in connection with bioreactor 130 of FIG. 1. The fermentation is typically conducted as a continuous fermentation as the biocatalyst is retained in bioreactor 320. Bioreactor 120 is maintained under suitable metabolic conditions The conversion of ethanol to higher organic product can vary widely depending upon the operator's objectives. Thus, the production of the higher organic product can be adjusted by changing the amount of side draw taken from beer still 308 and the conditions, including residence time, in bioreactor 320. Often the ethanol conversion to higher organic product is between about 10 and 80 percent, say, 20 to 70, percent. Since ethanol is a sought product of the processes of this invention, low conversions of ethanol to higher organic product may often be acceptable, and in some instances, desirable, to balance product mix.

Bioreactor 320 generates a bioconversion effluent containing higher organic product, ethanol and water. The bioconversion effluent can be directed back to beer still 308 where beer still 308 has the capability of recovering the higher organic product. Higher organic product may be recovered via line 314 from beer still 308. In such a mode of operation, bioconversion effluent is passed via line 324 to line 338 to beer still 308. The location, or locations, that the returned bioconversion effluent enters beer still 308 are numerous and often depend upon the design of beer still 308 and the hydraulic load. For instance, the bioconversion effluent can be introduced into the bottom portion of the still or at or slightly above or below the point that the side draw is taken from beer still 308. Where the beer still comprises multiple effects, the bioconversion effluent may be introduced into a subsequent effect to the effect from which the side draw is taken. The point of return of the bioconversion effluent can also serve to enable a recycle of unreacted ethanol to the side drawn.

In addition or alternatively, bioconversion effluent from bioreactor 320 may be passed via line 326 to recovery unit 328. The use of recovery unit 328 is particularly useful where the higher organic product is not feasibly recovered or recovered in desired purity in beer still 308. Recovery unit 328 may be of any suitable design, including, but not limited to, Typical Separation Techniques.

Higher organic product is provided by line 330 from recovery unit 328. Unreacted ethanol and water exit recovery unit 328 via line 332. If needed, a portion of the ethanol and water can be purged via line 334, e.g., to prevent the build-up of undesirable metabolites. However, at least a portion of the ethanol and water are returned to beer still 308 via line 336 and 338. Often at least about 50, and preferably at least about 70, percent of each of the water and ethanol in the bioconversion effluent, is returned to beer still 108.

Biocatalyst

A. Biocatalyst Overview

The biocatalysts of this invention have a polymeric structure (matrix) defining interconnected major cavities, i.e., are open, porous matrices, in which the microorganisms are metabolically retained in the interior of the matrices, that is, the microorganisms promote the adherence rather than being physically restrained by an external structure. In the biocatalysts of this invention, the microorganisms and their communities, inter alia, regulate their population. Also, in conjunction with the sensed nature of the microenvironment in the matrices, it is believed that the microorganisms establish a spatial relationship among the members of the community.

The microorganisms that are retained in the matrices have the ability to form an exo-network. The quiescent nature of the cavities facilitate forming and then maintaining any formed exo-network. A discernable exo-network is not believed essential to achieving phenotypic alterations in the microorganism population such as population modulation and metabolic shift. Where an exo-network develops, often strands of EPS interconnect proximate microorganisms and connect microorganisms to the surface and form the exo-network. In some instances, the microorganisms form thin biofilms and these thin biofilms are encompassed in the exo-network. The biocatalysts have a substantial absence of biofilms in their interiors that are larger than thin biofilms. Hence, any biofilms that may ultimately form in the biocatalysts are relatively thin, e.g., up to about 10, and preferably up to about 2 or 5, microns in thickness, and stable in size. Thus, each thin biofilm is often only a few cells and is connected in an exo-network.

A communication among the microorganisms is believed to occur through emitting chemical agents, including, but not limited to, autoinducers, and communication includes communications for community behavior and for signaling. Often, the preparation of the biocatalysts used in the processes of this invention can result in a population of microorganisms being initially located in the interior of the biocatalyst that is substantially that which would exist at the steady-state level. At these densities of microorganisms in the biocatalysts, community communications are facilitated which are believed to commence during the formation of the biocatalysts, and phenotypic shifts occur to enable the metabolic retention and modulate the population of microorganisms.

Another phenotypic alteration occurring in the biocatalysts, which is believed to be a result of this communication, is a metabolic shift, i.e., the metabolic functions of the community towards reproduction are diminished and the sought bioconversion continues. The population of microorganisms in the biocatalyst may tend to have an old average age due to this shift in the metabolic activity. Older microorganisms also tend to provide a more robust and sustainable performance as compared to younger cells as the older cells have adapted to the operating conditions.

Additional benefits of this communication can be an increase in community-level strength or fitness exhibited by the community in warding off adventitious microorganisms and maintaining strain-type uniformity. In some instances, the microorganisms during use of the biocatalyst may undergo natural selection to cause the strain-type in the community to become heartier or provide another benefit for the survival of the community of microorganisms. In some instances, the communication among the microorganisms may permit the population of microorganisms to exhibit multicellularity or multicellular-like behaviors. Thus the population of microorganisms in a biocatalyst of this invention may have microorganisms adapting to different circumstances but yet working in unison for the benefit of the community.

In some instances the porous matrix may provide modulation of the substrate and nutrients to the microorganisms to effect to optimize metabolic pathways involving substrates that are available, and these pathways may or may not be the primarily used pathways where ample substrate and other nutrients are available. Accordingly, microorganisms in the biocatalysts may exhibit enhanced bioactivity for a primarily used pathway or metabolic activity that is normally repressed.

It is also believed that the microenvironments may promote genetic exchange or horizontal gene transfer. Conjugation or bacterial mating may also be facilitated, including the transfer of plasmids and chromosomal elements. Moreover, where microorganisms lyse, strands of DNA and RNA in the microenvironments are more readily accessible to be taken up by microorganisms in these microenvironments. These phenomena can enhance the functional abilities of the microorganisms.

The biocatalysts exhibit an increased tolerance to toxins. In some instances, communications among microorganisms and the exo-network may facilitate the population establishing defenses against toxins. The community response to the presence of toxins has been observed in the biocatalysts of this invention. For instance, the biocatalysts survive the addition of toxins such as ethanol and sodium hypochlorite and the original bioconversion activity is quickly recovered thus indicating the survival of essentially the entire community.

In summary, due to the microenvironments in the biocatalyst, communication among the microorganisms and the phenotypic alterations undergone by the microorganisms, the biocatalysts provide a number of process-related advantages including, but not limited to, no solid debris being generated,
the potential for high densities of bioactive material in a bioreactor,
stable population of microorganisms and bioactivity over extended periods of time,
metabolic shift of microorganisms towards production rather than growth and carbon flow shift,
ability of microorganisms to undergo essential stasis for extended durations,
ability to quickly respond to changes in substrate rate of supply and concentration,
attenuation of diauxic growth,
enhanced control and modulation of pH and redox balances in the microenvironment of the biocatalyst,
greater tolerance to substrate, bioproduct and contaminants,
ability to bioconvert substrate at ultralow concentrations,
ability to use slower growing and less robust microorganisms and increased resistance to competitiveness,
enhanced microorganism strain purity capabilities,
ability to be subjected to in situ antimicrobial treatment,
ability to quickly start a bioreactor since the density of bioactive material required at full operation is contained in the biocatalyst,
ability to contact biocatalyst with gas phase substrate, and
ease of separation of bioproduct from biocatalyst thereby facilitating continuous operations.

If desired, the biocatalysts, where containing microorganisms, may be treated to enhance the formation of the exo-network, and if desired, thin biofilms, prior to use in the metabolic process. However, performance of the porous matrices is not generally dependent upon the extent of exo-network formation, and often bioconversion activities remain relatively unchanged between the time before the microorganisms have attached to the polymeric structure and the time when extensive exo-network structures have been generated.

B. Physical Description of the Porous Matrices

The biocatalysts of this invention comprise a matrix having open, porous interior structure with bioactive material irreversibly retained in at least the major cavities of the matrix.

The matrices may be a self-supporting structure or may be placed on or in a preformed structure such as a film, fiber or hollow fiber, or shaped article. The preformed structure may be constructed of any suitable material including, but not limited to, metal, ceramic, polymer, glass, wood, composite material, natural fiber, stone, and carbon. Where self-supporting, the matrices are often in the form of sheets, cylinders, plural lobal structures such as trilobal extrudates, hollow fibers, or beads which may be spherical, oblong, or free-form. The matrices, whether self-supporting or placed on or in a preformed structure, preferably have a thickness or axial dimension of less than about 5, preferably less than about 2, say, between about 0.01 to 1, centimeters.

The porous matrices may have an isotropic or, preferably, an anisotropic structure with the exterior portion of the cross section having the densest structure. The major cavities, even if an anisotropic structure exists, may be relatively uniform in size throughout the interior of the matrix or the size of the major cavities, and their frequency, may vary over the cross-section of the biocatalyst.

The biocatalyst of this invention has major cavities, that is, open, interconnected regions of between about 5 or 10 to 70 or 100 microns in the smallest dimension (excluding any microorganisms contained therein). For the purposes of ascertaining dimensions, the dimensions of the microorganisms includes any mass in the exo-network. In many instances, the major cavities have nominal major dimensions of less than about 300, preferably less than about 200, microns, and sometimes a smallest dimension of at least about 10 microns. Often the biocatalyst contains smaller channels and cavities which are in open communication with the major cavities. Frequently the smaller channels have a maximum cross-sectional diameter of between about 0.5 to 20, e.g., 1 to 5 or 10, microns. The cumulative volume of major cavities, excluding the volume occupied by microorganisms and mass associated with the microorganisms, to the volume of the biocatalyst is generally in the range of about 40 or 50 to 70 or 99, volume percent. In many instances, the major cavities constitute less than about 70 percent of the volume of the fully catalyst with the remainder constituting the smaller channels and pores. The volume fraction of the biocatalyst that constitute the major cavities can be estimated from its cross-section. The cross section may be observed via any suitable microscopic technique, e.g., scanning electron microscopy and high powered optical microscopy. The total pore volume for the matrices can be estimated from the volumetric measurement of the matrices and the amount and density of polymer, and any other solids used to make the matrices.

The biocatalyst is characterized by having high internal surface areas, often in excess of at least about 1 and sometimes at least about 10, square meter per gram. In some instances, the volume of water that can be held by a fully hydrated biocatalyst (excluding the volume of the microorganisms) is in the range of 90 to 99 or more, percent. Preferably the biocatalyst exhibits a Hydration Expansion Volume (HEV) of at least about 1000, frequently at least about 5000, preferably at least about 20,000, and sometimes between 50,000 and 200,000, percent. Usually the type of polymer selected and the void volume percent of the matrices are such that the matrices have adequate strength to enable handling, storage and use in a bioconversion process.

The porous matrices may or may not have an exterior skin. Preferably the matrices have an exterior skin to assist in modulating the influx and efflux of components to and from the interior channels of the porous matrix. Also, since the skin is highly hydrophilic, and additional benefit is obtained as contaminating or adventitious microorganisms have difficulties in establishing a strong biofilm on the exterior of the biocatalyst. These contaminating microorganisms are often subject to removal under even low physical forces such as by the flow of fluid around the biocatalysts. Thus, the fouling of the biocatalyst can be substantially eliminated or mitigated by washing or by fluid flows during use.

Where present, the skin typically has pores of an average diameter of between about 1 and 10, preferably 2 to 7, microns in average diameter. The pores may comprise about 1 to 30, say, 2 to 20, percent of the external surface area. The external skin, in addition to providing a barrier to entry of adventitious microorganisms into the interior of the biocatalyst, is preferably relatively smooth to reduce the adhesion of microorganisms to the external side of the skin through physical forces such as fluid flow and contact with other solid surfaces. Often, the skin is substantially devoid of anomalies, other than pores, greater than about 2 or 3 microns. Where a skin is present, its thickness is usually less than about 50, say, between about 1 and 25, microns. It should be understood that the thickness of the skin can be difficult to discern where the porous matrix has an anisotropic structure with the densest structure being at the exterior of the matrix.

A high concentration of isolated enzyme and or density of microorganisms can exist at steady-state operation within the biocatalysts. The combination of the flow channels and the high permeability of the polymeric structure defining the channels enable viable microorganism population throughout the matrix, albeit with a plurality of unique microenvironments and nano-environments. In some instances, when the bioactive material comprises microorganisms, the cell density based upon the volume of the matrices is at least about 100 grams per liter, preferably at least about 200, and often between about 250 and 750, grams per liter.

Polysaccharide-Containing Biocatalysts

Solid polysaccharide in the interior of the biocatalyst, the viability of the microorganism can be maintained. A solid polysaccharide is a polysaccharide that does not dissolve in water at 50° C. Typically solid polysaccharides are not usable by most microorganisms. Often, the solid polysaccharide is provided in an amount of at least about 0.1, say, at least about 0.2 to 100, gram per gram of cells retained in the biocatalyst, and sometimes the biocatalyst contains between 25 and 500 grams of polysaccharide per liter of volume of fully hydrated biocatalyst. The solid polysaccharide particles preferably have a major dimension of less than about 50, preferably less than about 20, often between about 0.1 to 5, microns. The solid polysaccharide particles are preferably granular and often have an aspect ratio of minimum cross-sectional dimension to maximum cross sectional dimension of between about 1:10 to 1:1, say 1:2 to 1:1.

The polysaccharide may be from any suitable source including, but not limited to, cellulosic polysaccharides or starches. Polysaccharides are carbohydrates characterized by repeating units linked together by glycosidic bonds and are substantially insoluble in water. Polysaccharides may be homopolysaccharides or heteropolysaccharides and typically have a degree of polymerization of between about 200 and 15,000 or more, preferably between about 200 and 5000. The preferred polysaccharides are those in which about 10, more preferably, at least about 20, percent of the repeating units are amylose (D-glucose units). Most preferably the polysaccharide has at least about 20, more preferably, at least about 30, percent of the repeating units being amylose. The polysaccharides may or may not be functionalized, e.g., with acetate, sulfate, phosphate, pyruvyl cyclic acetal, and the like, but such functionalization should not render the polysaccharide water soluble at temperatures below about 50° C. A preferred class of polysaccharides is starches.

Sources of polysaccharides include naturally occurring and synthetic (e.g., polydextrose) polysaccharides. Various plant based materials providing polysaccharides include but are not limited to woody plant materials providing cellulose and hemicellulose, and wheat, barley, potato, sweet potato, tapioca, corn, maize, cassava, milo, rye and brans typically providing starches.

Solid Sorbent-Containing Biocatalysts

The biocatalysts may contain a solid sorbent. The solid sorbent may be the hydrophilic polymer forming the structure or may be a particulate, i.e., a distinct solid structure regardless of shape) contained in the solid structure. The sorbent may be any suitable solid sorbent for the substrate or nutrients or other chemical influencing the sought metabolic activity such as, but not limited to, co-metabolites, inducers, and promoters or for components that may be adverse to the microorganisms such as, and not in limitation, toxins, phages, bioproducts and by-products. The solid sorbent is typically an adsorbent where the sorption occurs on the surface of the sorbent. The particulate solid sorbents are preferably nano materials having a major dimension less than about 5 microns, preferably, between about 5 nanometers to 3 microns. Where the solid sorbent is composed of polymer, the solid structure may be essentially entirely composed of the polymer or may be a block copolymer or polymeric mixture constituting between about 5 and 90 mass percent of the solid structure (excluding water). Where the solid sorbent is a separate particulate in the biocatalyst, the biocatalyst may comprise between about 5 to 90 mass percent of the mass of the biocatalyst (excluding water and microorganisms but including both the hydrophilic polymer and the particulates). More than one solid sorbent may be used in a biocatalyst. Preferably the solid sorbent is relatively uniformly dispersed throughout the interior of the biocatalyst although the solid sorbent may have a varying distribution within the biocatalyst. Where the distribution varies, the regions with the higher concentration of solid sorbent often are found toward the surface of the biocatalyst.

Where a particulate sorbent is used, the sorbent comprises an organic or inorganic material having the sought sorptive capacity. Examples of solid sorbents include, without limitation, polymeric materials, especially with polar moieties, carbon (including but not limited to activated carbon), silica (including but not limited to fumed silica), silicates, clays, molecular sieves, and the like. The molecular sieves include, but are not limited to zeolites and synthetic crystalline structures containing oxides and phosphates of one or more of silicon, aluminum, titanium, copper, cobalt, vanadium, titanium, chromium, iron, nickel, and the like. The sorptive properties may comprise one or more of physical or chemical or quasi-chemical sorption on the surface of the solid sorbent. Thus, surface area and structure may influence the sorptive properties of some solid sorbents. Frequently the solid sorbents are porous and thus provide high surface area and physical sorptive capabilities. Often the pores in the solid sorbents are in the range of about 0.3 to 2 nanometers in effective diameter.

The solid sorbent may be incorporated into the polymeric structure in any convenient manner, preferably during the preparation of the biocatalyst.

Phosphorescent-Containing Biocatalysts

Another preferred aspect of the invention pertains to biocatalysts containing phosphorescent material and photosynthetic microorganisms, i.e., microorganisms that uses light energy in a metabolic process. Preferably the microorganism is an algae, most preferably a microalgae, or cyanobacteria.

The bioactivity of photosynthetic microorganisms can be enhanced to produce expressed bioproduct using broad-based light source such as sunlight. In accordance with the invention, the photosynthetic microorganisms are irreversibly retained in biocatalysts in which the interior of the biocatalyst contains phosphorescent material capable of shifting UV light to light having a wavelength of between about 400 and 800, preferably between about 450 and 650, nm and is capable of exhibiting persistence, with the emission of the light often lasting for at least about 5 seconds. A phosphorescent material is a material that has the ability to be excited by electromagnetic radiation into an excited state, but the stored energy is released gradually. Emissions from phosphorescent materials have persistence, that is, emissions from such materials can last for seconds, minutes or even hours after the excitation source is removed. A luminescent material is a material capable of emitting electromagnetic radiation after being excited into an excited state. Persistence is the time it takes, after discontinuing irradiation, for photoluminescent emissions emanating from a photoluminescent object to decrease to the threshold detectability.

The persistence of the radiation enables the microorganisms to be cycled in and out of a region of the culture liquid exposed to the light source and still be productive. With longer persistence durations, the photosynthetic microorganisms can continue photo-bioconversion in the absence of or reduction in light intensity. The ability of the biocatalysts to maintain photosynthetic activity over extended periods of time, often at least about 30 days, and in some instances for at least one year, the cost of the phosphorescent materials is well offset by the increased production, reduced footprint of the bioreactor, and facilitated bioproduct recovery.

The biocatalyst, being highly hydrated is a significant distributor of light radiation to photosynthetic microorganisms retained in the interior of the biocatalyst and also serves to protect the microorganism from photorespiration. The solid debris in the culture liquid (an aqueous solution comprising nutrients for metabolic processes) can be materially reduced, if not essentially eliminated, due to the microorganisms being irreversibly retained in the biocatalyst. Thus the turbidity is reduced and a given light intensity can thus be found at a greater depth in the culture liquid. These advantages provided by the biocatalysts of this invention can be realized in any photosynthetic process regardless of whether or not a phosphorescent material is used.

Examples of phosphorescent materials include, but are not limited to, phosphorescent materials are metal sulfide phosphors such as ZnCdS:Cu:Al, ZnCdS:Ag:Al, ZnS:Ag:Al, ZnS:Cu:Al as described in U.S. Pat. No. 3,595,804 and metal sulfides that are co-activated with rare earth elements such as those describe in U.S. Pat. No. 3,957,678. Phosphors that are higher in luminous intensity and longer in luminous persistence than the metal sulfide pigments include compositions comprising a host material that is generally an alkaline earth aluminate, or an alkaline earth silicate. The host materials generally comprise Europium as an activator and often comprise one or more co-activators such as elements of the Lanthanide series (e.g. lanthanum, cerium, praseodymium, neodymium, samarium, gadolinium, terbium, dysprosium, holmium, erbium, thulium, ytterbium, and lutetium), tin, manganese, yttrium, or bismuth. Examples of such phosphors are described in U.S. Pat. No. 5,424,006.

High emission intensity and persistence phosphorescent materials can be alkaline earth aluminate oxides having the formula $MO_mAl_2O_3:Eu^{2+}, R^{3+}$ wherein m is a number ranging from 1.6 to about 2.2, M is an alkaline earth metal (strontium, calcium or barium), $Eu^{2+}$ is an activator, and R is one or more trivalent rare earth materials of the lanthanide series (e.g. lanthanum, cerium, praseodymium, neodymium, samarium, gadolinium, terbium, dysprosium, holmium, erbium, thulium, ytterbium, lutetium), yttrium or bismuth co-activators. Examples of such phosphors are described in U.S. Pat. No. 6,117,362. Phosphorescent materials also include alkaline earth aluminate oxides having the formula $M_kAl_2O_4:2xEu^{2+}, 2yR^{3+}$ wherein k=1−2x−2y, x is a number ranging from about 0.0001 to about 0.05, y is a number ranging from x to 3x, M is an alkaline earth metal (strontium, calcium or barium), $Eu^{2+}$ is an activator, and R is one or more trivalent rare earth materials (e.g. lanthanum, cerium, praseodymium, neodymium, samarium, gadolinium, terbium, dysprosium, holmium, erbium, thulium, ytterbium, lutetium), yttrium or bismuth co-activators. See U.S. Pat. No. 6,267,911B1. Phosphorescent materials also include those in which a portion of the $Al^{3+}$ in the host matrix is replaced with divalent ions such as $Mg^{2+}$ or $Zn^{2+}$ and those in which the alkaline earth metal ion ($M^{2+}$) is replaced with a monovalent alkali metal ion such as $Li^+$, $Na^+$, $K^+$, $Cs^+$ or $Rb^+$ such as described in U.S. Pat. Nos. 6,117,362 and 6,267,911B1.

High intensity and high persistence silicates have been disclosed in U.S. Pat. No. 5,839,718, such as Sr.BaO.Mg.MO.SiGe:Eu:Ln wherein M is beryllium, zinc or cadmium and Ln is chosen from the group consisting of the rare earth materials, the group 3A elements, scandium, titanium, vanadium, chromium, manganese, yttrium, zirconium, niobium, molybdenum, hafnium, tantalum, tungsten, indium, thallium, phosphorous, arsenic, antimony, bismuth, tin, and lead. Particularly useful are dysprosium, neodymium, thulium, tin, indium, and bismuth. X in these compounds is at least one halide atom.

Other phosphorescent materials include alkaline earth aluminates of the formula $MO.Al_2O_3.B_2O_3:R$ wherein M is a combination of more than one alkaline earth metal (strontium, calcium or barium or combinations thereof) and R is a combination of $Eu^{2+}$ activator, and at least one trivalent rare earth material co-activator, (e.g. lanthanum, cerium, praseodymium, neodymium, samarium, gadolinium, terbium, dysprosium, holmium, erbium, thulium, ytterbium, lutetium), bismuth or manganese. Examples of such phosphors can be found in U.S. Pat. No. 5,885,483. Alkaline earth aluminates of the type $MAl_2O_4$, which are described in U.S. Pat. No. 5,424,006, may also find application as may phosphorescent materials comprising a donor system and an acceptor system such as described in U.S. Pat. No. 6,953,536 B2.

As can be appreciated, many other phosphors can find application. See, for instance, Yen and Weber, Inorganic Phosphors: Compositions, Preparation and Optical Properties, CRC Press, 2004.

The phosphorescent material may be a discrete particle or may be a particle having a coating to facilitate incorporation and retention in the polymer forming the matrix. The particles may be of any suitable shape. Generally the maximum dimension of the of the particles is less than about 1 millimeter, preferably less than about 0.1 millimeter. The particles may be nanoparticles.

The persistence time exhibited by the phosphorescent materials can range from a short duration, e.g., about 5 to 10 seconds, to as much as 10 or 20 hours or more and will be dependent upon the phosphorescent material used. Preferred phosphorescent materials exhibit a persistence of at least about one minute. The intensity of the emitted radiation from the polymer of the matrices will, in part, depend upon the concentration of the phosphorescent material in the polymer and the nature of the phosphorescent material. Typically the phosphorescent material is provided in an amount of at least about 0.1, say, between 0.2 and 5 or 10, mass percent of the polymer (non-hydrated) in the biocatalyst. One or more phosphorescent materials may be used in the biocatalyst. Where more than one phosphorescent material are used, the combination may be selected to provide one or more of wave shifting from different light wavelengths contained in the band width of the radiation source and providing differing persistence times. In preferred embodiments the phosphorescent materials are in the form of nanoparticles, e.g., having a major dimension of between about 10 nm and 10 μm. In some instances, it may be desired to coat the phosphorescent materials with a compatibilizing agent to facilitate incorporation of the phosphorescent material within the polymer. Compatibilizing agents include, but are not limited to, molecules having one or more of hydroxyl, thiol, silyl, carboxyl, or phosphoryl groups.

Enzyme-Containing Biocatalysts

In another aspect, the biocatalysts can contain, in addition to the microorganisms, one or more extracellular enzymes in the interior of the biocatalyst to cause a catalytic change to a component which may be substrate or other nutrients, or a bioproduct or by-product or co-product of the microorganisms, or may be a toxin, phage or the like. Typically extracellular enzymes bond or adhere to solid surfaces, such as the hydrophilic polymer, solid additives, cell walls and extracellular polymeric substance. Hence, the enzymes can be substantially irreversibly retained in the interior of the biocatalyst. Due to the structure of the biocatalysts of this invention, the microorganisms and the enzymes can be in close proximity and thus effective, cooperative bioconversions can be obtained. The association of the enzymes with the interior surfaces of the biocatalyst typically increases the resistance of the enzyme or enzymes to denaturation due to changes in temperature, pH, or other factors related to thermal or operational stability of the enzymes. Also, by being retained in the biocatalyst, the use of the enzyme in a bioreactor is facilitated and undesirable post-reactions can be mitigated.

Examples of enzymes include, but are not limited to, one or more of oxidorectases, transferases, hydrolases, lyases, isomerases, and ligases. The enzymes may cause one or more metabolic conversions. For instance, an enzyme may metabolize a component in the feed to provide an intermediate for use by the microorganisms in the biocatalyst. An enzyme may be used to metabolize a metabolite of the microorganism to provide a sought bioproduct. An enzyme may be used to metabolize a component in the feed or a co-metabolite from the microorganism that may be adverse to the microorganism into a metabolite that is less adverse to the microorganism. If desired, two or more different enzymes can be used to effect a series of metabolic conversions on a component in the feed or a metabolite from the microorganism.

Representative enzymes include, without limitation: cellulase, cellobiohydrolase (e.g., CBHI, CBHII), alcohol dehydrogenase (A, B, and C), acetaldehyde dehydrogenase, amylase, alpha amylase, glucoamylase, beta glucanase, beta glucosidase, invertase, endoglucanase (e.g., EGI, EGII, EGIII), lactase, hemicellulase, pectinase, hydrogenase, pullulanase, phytase, a hydrolase, a lipase, polysaccharase, ligninase, Accellerase® 1000, Accellerase® 1500, Accellerase® DUET, Accellerase® TRIO, or Cellic CTec2 enzymes, phosphoglucose isomerase, inositol-1-phosphate synthase, inositol monophosphatase, myo-inositol dehydrogenase, myo-inosose-2-dehydratase, inositol 2-dehydrogenase, deoxy-D-gluconate isomerase, kinase, 5-dehydro-2-deoxygluconokinase, deoxyphophogluconate aldolase, 3-hydroxy acid dehydrogenase, isomerase, topoisomerase, dehydratase, monosaccharide dehydrogenase, aldolase, phosphatase, a protease, DNase, alginate lyase, laminarinase, endoglucanase, L-butanediol dehydrogenase, acetoin reductase, 3-hydroxyacyl-CoA dehydrogenase, or cis-aconitate decarboxylase. The enzymes include those described by Heinzelman et al. (2009) PNAS 106: 5610-5615, herein incorporated by reference in its entirety.

The enzymes may be bound to the precursor for the hydrophilic polymer of the biocatalyst prior to the formation of the biocatalyst or may be introduced during the preparation of the biocatalyst, e.g., by addition to the liquid medium for forming the biocatalyst. There are many methods that would be known to one of skill in the art for providing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process. Various methods are described in Methods in Enzymology, Immobilized Enzymes and Cells, Part C. 1987. Academic Press. Edited by S. P. Colowick and N. O. Kaplan. Volume 136; Immobilization of Enzymes and Cells. 1997. Humana Press. Edited by G. F. Bickerstaff. Series: Methods in Biotechnology, Edited by J. M. Walker; DiCosimo, R., McAuliffe, J., Poulose, A. J. Bohlmann, G. 2012. Industrial use of immobilized enzymes. Chem. Soc. Rev.; and Immobilized Enzymes: Methods and Applications. Wilhelm Tischer and Frank Wedekind, Topics in Current Chemistry, Vol. 200. Page 95-126.

C. Methods for Making Biocatalysts

The components, including bioactive materials, used to make the biocatalysts and the process conditions used for the preparation of the biocatalysts are not critical to the broad aspects of this invention and may vary widely as is well understood in the art once understanding the principles described above. In any event, the components and process conditions for making the biocatalysts with the irreversibly, metabolically retained microorganisms should not adversely affect the microorganisms.

The biocatalysts may be prepared from a liquid medium containing the bioactive material and solubilized precursor for the hydrophilic polymer which may be one or more of a polymerizable or solidifiable component or a solid that is fusible or bondable to form the matrix. Aqueous media are most often used due to the compatibility of most microorganisms and enzymes with water. However, with bioactive materials that tolerate other liquids, such liquids can be used to make all or a portion of the liquid medium. Examples of such other liquids include, but are not limited to liquid hydrocarbons, peroxygenated liquids, liquid carboxy-containing compounds, and the like. Mixed liquid media can also be used to prepare the biocatalyst. The mixed media may comprise miscible or immiscible liquid phases. For instance, the bioactive material may be suspended in a dispersed, aqueous phase and the polymerizable or solidifiable component may be contained in a continuous solvent phase.

The liquid medium used to prepare the biocatalyst may contain more than one type of microorganism, especially where the microorganisms do not significantly compete for the same substrate, and may contain one or more isolated enzymes or functional additives such as polysaccharide, solid sorbent and phosphorescent materials, as described above. Preferably, the biocatalysts contain a single type of microorganism. The concentration of the microorganisms in the liquid medium used to make the biocatalysts should at least be about 60 grams per liter. As discussed above, the concentration of microorganisms should preferably approximate the sought density of microorganisms in the biocatalyst. The relative amounts of microorganism and polymeric material in forming the biocatalyst can vary widely. The growth of the population of microorganisms post formation of the biocatalyst is contemplated as well as the potential for damage to some of the population of microorganisms during the biocatalyst-forming process. Nevertheless, higher microorganism concentrations are generally preferred, e.g., at least about 100 grams per liter, preferably at least about 200, and often between about 250 and 750, grams per liter of the liquid medium used to make the biocatalysts.

Any suitable process may be used to solidify or polymerize the polymeric material or to adhere or fuse particles to form the open, porous polymeric matrix with microorganism irreversibly retained therein. The conditions of suitable processes should not unduly adversely affect the microorganisms. As microorganisms differ in tolerance to temperatures, pressures and the presence of other chemicals, some matrix-forming processes may be more advantageous for one type of microorganism than for another type of microorganism.

Preferably the polymeric matrix is formed from solidification of a high molecular weight material, by polymerization or by cross-linking of prepolymer in manner that a population of microorganisms is provided in the interior of the biocatalyst as it is being formed. Exemplary of processes include solution polymerization, slurry polymerization (characterized by having two or more initial phases), and solidification by cooling or removal of solvent.

The biocatalysts may be formed in situ in the liquid medium by subjecting the medium to solidification conditions (such as cooling or evaporation) or adding a component to cause a polymerization or cross-linking or agglomeration of solids to occur to form a solid structure such as a catalyst, cross-linking agent or coagulating agent. Alternatively, the liquid medium may be extruded into a solution containing a solidification agent such as a catalyst, cross-linking or coagulating agent or coated onto a substrate and then the composite subjected to conditions to form the solid biocatalyst.

Polymeric materials used to make the biocatalysts may have an organic or inorganic backbone but have sufficient hydrophilic moieties to provide a highly hydrophilic polymer which when incorporated into the matrices exhibits sufficient water sorption properties to provide the sought Hydration Expansion Volume of the biocatalyst. Polymeric materials are also intended to include high molecular weight substances such as waxes (whether or not prepared by a polymerization process), oligomers and the like so long as they form biocatalysts that remain solid under the conditions of the bioconversion process intended for their use and have sufficient hydrophilic properties that the Hydration Expansion Volume can be achieved. As stated above, it is not essential that polymeric materials become cross-linked or further polymerized in forming the polymeric matrix.

Examples of polymeric materials include homopolymers and copolymers which may or may not be cross-linked and include condensation and addition polymers that provide high hydrophilicity and enable the Hydration Expansion Volumes to be obtained. The polymer may be a homopolymer or a copolymer, say, of a hydrophilic moiety and a more hydrophobic moiety. The molecular weight and molecular weight distribution are preferably selected to provide the combination of hydrophilicity and strength as is known in the art. The polymers may be functionalized with hydrophilic moieties to enhance hydrophilicity. Examples of hydrophilic moieties include, but are not limited to hydroxyl, alkoxyl, acyl, carboxyl, amido, and oxyanions of one or more of titanium, molybdenum, phosphorus, sulfur and nitrogen such as phosphates, phosphonates, sulfates, sulfonates, and nitrates, and the hydrophilic moieties may be further substituted with hydrophilic moieties such as hydroxyalkoxides, acetylacetonate, and the like. Typically the polymers contain carbonyl and hydroxyl groups, especially at some adjacent hydrophilic moieties such as glycol moieties. In some instances, the backbone of the polymer contains ether oxygens to enhance hydrophilicity. In some instances, the atomic ratio of oxygen to carbon in the polymer is between about 0.3:1 to 5:1.

Polymers which may find use in forming the matrices include functionalized or non-functionalized polyacrylamides, polyvinyl alcohols, polyetherketones, polyurethanes, polycarbonates, polysulfones, polysulfides, polysilicones, olefinic polymers such as polyethylene, polypropylene, polybutadiene, rubbers, and polystyrene, nylons, polythyloxazyoline, polyethylene glycol, polysaccharides such as sodium alginate, carageenan, agar, hyaluronic acid, chondroitin sulfate, dextran, dextran sulfate, heparin, heparin sulfate, heparan sulfate, chitosan, gellan gum, xanthan gum, guar gum, water soluble cellulose derivatives and carrageenan, and proteins such as gelatin, collagen and albumin, which may be polymers, prepolymers or oligomers, and polymers and copolymers from the following monomers, oligomers and prepolymers:

monomethacrylates such as polyethylene glycol monomethacrylate, polypropylene glycol monomethacrylate, polypropylene glycol monomethacrylate, methoxydiethylene glycol methacrylate, methoxypolyethylene glycol methacrylate, methacryloyloxyethyl hydrogen phthalate, methacryloyloxyethyl hydrogen succinate, 3-chloro-2-hydroxypropyl methacrylate, stearyl methacrylate, 2-hydroxy methacrylate, and ethyl methacrylate;

monoacrylates such as 2-hydroxyethyl acrylate, 2-hydroxypropyl acrylate, isobutyl acrylate, t-butyl acrylate, isooctyl acrylate, lauryl acrylate, stearyl acrylate, isobornyl acrylate, cyclohexyl acrylate, methoxytriethylene glycol acrylate, 2-ethoxyethyl acrylate, tetrahydrofurfuryl acrylate, phenoxyethyl acrylate, nonylphenoxypolyethylene glycol acrylate, nonylphenoxypolypropylene glycol acrylate, silicon-modified acrylate, polypropylene glycol monoacrylate, phenoxyethyl acrylate, phenoxydiethylene glycol acrylate, phenoxypolyethylene glycol acrylate, methoxypolyethylene glycol acrylate, acryloyloxyethyl hydrogen succinate, and lauryl acrylate;

dimethacrylates such as 1,3-butylene glycol dimethacrylate, 1,4-butanediol dimethacrylate, ethylene glycol dimethacrylate, diethylene glycol dimethacrylate, triethylene glycol dimethacrylate, polyethylene glycol dimethacrylate, butylene glycol dimethacrylate, hexanediol dimethacrylate, neopentyl glycol dimethacrylate, polyprene glycol dimethacrylate, 2-hydroxy-1,3-dimethacryloxypropane, 2,2-bis-4-methacryloxyethoxyphenylpropane, 3,2-bis-4-methacryloxydiethoxyphenylpropane, and 2,2-bis-4-methacryloxypolyethoxyphenylpropane;

diacrylates such as ethoxylated neopentyl glycol diacrylate, polyethylene glycol diacrylate, 1,6-hexanediol diacrylate, neopentyl glycol diacrylate, tripropylene glycol diacrylate, polypropylene glycol diacrylate, 2,2-bis-4-acryloxyethoxyphenylpropane, 2-hydroxy-1-acryloxy-3-methacryloxypropane; trimethacrylates such as trimethylolpropane trimethacrylate; triacrylates such as trimethylolpropane triacrylate, pentaerythritol triacrylate, trimethylolpropane EO-added triacrylate, glycerol PO-added triacrylate, and ethoxylated trimethylolpropane triacrylate; tetraacrylates such as pentaerythritol tetraacrylate, ethoxylated pentaerythritol tetraacrylate, propoxylated pentaerythritol tetraacrylate, and ditrimethylolpropane tetraacrylate;

urethane acrylates such as urethane acrylate, urethane dimethyl acrylate, and urethane trimethyl acrylate;

amino-containing moieties such as 2-aminoethyl acrylate, 2-aminoethyl methacrylate, aminoethyl methacrylate, dimethyl aminoethyl methacrylate, monomethyl aminoethyl methacrylate, t-butylaminoethylmethacrylate, p-aminostyrene, o-aminostyrene, 2-amino-4-vinyltoluene, dimethylaminoethyl acrylate, diethylaminoethyl acrylate, piperidinoethyl ethyl acrylate, piperidinoethyl methacrylate, morpholinoethyl acrylate, morpholinoethyl methacrylate, 2-vinyl pyridine, 3-vinyl pyridine, 2-ethyl-5-vinyl pyridine, dimethylaminopropylethyl acrylate, dimethylaminopropylethyl methacrylate, 2-vinyl pyrrolidone, 3-vinyl pyrrolidone, dimethylaminoethyl vinyl ether, dimethylaminoethyl vinyl sulfide, diethylaminoethyl vinyl ether, 2-pyrrolidinoethyl acrylate, 2-pyrrolidinoethyl methacrylate, and other monomers such as acrylamide, acrylic acid, and dimethylacrylamide.

Not all the above listed polymers will be useful by themselves, but may be required to be functionalized or used to form a co-polymer with a highly hydrophilic polymer.

Cross linking agents, accelerators, polymerization catalysts, and other polymerization additives may be employed such as triethanolamine, triethylamine, ethanolamine, N-methyl diethanolamine, N,N-dimethyl benzylamine, dibenzyl amino, N-benzyl ethanolamine, N-isopropyl benzylamino, tetramethyl ethylenediamine, potassium persulfate, tetramethyl ethylenediamine, lysine, ornithine, histidine, arginine, N-vinyl pyrrolidinone, 2-vinyl pyridine, 1-vinyl imidazole, 9-vinyl carbazone, acrylic acid, and 2-allyl-2-methyl-1,3-cyclopentane dione. For polyvinyl alcohol polymers and copolymers, boric acid and phosphoric acid may be used in the preparation of polymeric matrices. As stated above, the amount of cross-linking agent may need to be limited to assure that the matrices retain high hydrophilicity and the ability to have a high Hydration Expansion Volume. The selection of the polymer and cross-linking agents and other additives to make porous matrices having the physical properties set forth above is within the level of the artisan in the art of water soluble and highly hydrophilic polymer synthesis.

The biocatalysts may be formed in the presence of other additives which may serve to enhance structural integrity or provide a beneficial activity for the microorganism such as attracting or sequestering components, providing nutrients, and the like. Additives can also be used to provide, for instance, a suitable density to be suspended in the aqueous medium rather than tending to float or sink in the broth. Typical additives include, but are not limited to, starch, glycogen, cellulose, lignin, chitin, collagen, keratin, clay, alumina, aluminosilicates, silica, aluminum phosphate, diatomaceous earth, carbon, polymer, polysaccharide and the like. These additives can be in the form of solids when the polymeric matrices are formed, and if so, are often in the range of about 0.01 to 100 microns in major dimension.

If desired, where the biocatalyst contains microorganisms, they may be subjected to stress as is known in the art. Stress may be one or more of starvation, chemical or physical conditions. Chemical stresses include toxins, antimicrobial agents, and inhibitory concentrations of compounds. Physical stresses include light intensity, UV light, temperature, mechanical agitation, pressure or compression, and desiccation or osmotic pressure. The stress may produce regulated biological reactions that protect the microorganisms from shock and the stress may allow the hardier microorganisms to survive while the weaker cells die.

Microorganisms

The biocatalyst comprises microorganisms, the microorganisms may be unicellular or may be multicellular that behaves as a single cell microorganism such as filamentous growth microorganisms and budding growth microorganisms. Often the cells of multicellular microorganisms have the capability to exist singularly. The microorganisms can be of any type, including, but not limited to, those microorganisms that are aerobes, anaerobes, facultative anaerobes, heterotrophs, autotrophs, photoautotrophs, photoheterotrophs, chemoautotrophs, and/or chemoheterotrophs. The cellular activity, including cell growth can be aerobic, microaerophilic, or anaerobic. The cells can be in any phase of growth, including lag (or conduction), exponential, transition, stationary, death, dormant, vegetative, sporulating, etc. The one or more microorganisms be a psychrophile (optimal growth at −10° C. to 25° C.), a mesophile (optimal growth at 20-50° C.), a thermophile (optimal growth 45° C. to 80° C.), or a hyperthermophile (optimal growth at 80° C. to 100° C.). The one or more microorganisms can be a gram-negative or gram-positive bacterium. A bacterium can be a cocci (spherical), bacilli (rod-like), or spirilla (spiral-shaped; e.g., vibrios or comma bacteria). The microorganisms can be phenotypically and genotypically diverse.

The microorganisms can be a wild-type (naturally occurring) microorganism or a recombinant (including, but not limited to genetically engineered microorganisms) microorganism. A recombinant microorganism can comprise one or more heterologous nucleic acid sequences (e.g., genes). One or more genes can be introduced into a microorganism used in the methods, compositions, or kits described herein, e.g., by homologous recombination. One or more genes can be introduction into a microorganism with, e.g., a vector. The one or more microorganisms can comprise one or more vectors. A vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain a means for self-replication. The vector can, when introduced into a host cell, integrate into the genome of the host cell and replicate together with the one or more chromosomes into which it has been integrated. Such a vector can comprise specific sequences that can allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants. Means of genetically manipulating organisms are described, e.g., Current Protocols in Molecular Biology, last updated Jul. 25, 2011, Wiley, Print ISSN: 1934-3639. In some embodiments, one or more genes involved in byproduct formation are deleted in a microorganism. In some embodiments, one or more genes involved in byproduct formation are not deleted. Nucleic acid introduced into a microorganism can be codon-optimized for the microorganism. A gene can be modified (e.g., mutated) to increase the activity of the resulting gene product (e.g., enzyme). Sought properties in wild-type or genetically modified microorganisms can often be enhanced through a natural modification process, or self-engineering process, involving multigenerational selective harvesting to obtain strain improvements such as microorganisms that exhibit enhanced properties such as robustness in an environment or bioactivity. See, for instance, Ben-Jacob, et al., Self-engineering capabilities of bacteria, J. R. Soc. Interface 2006, 3, doi: 10.1098/rsif.2005.0089, 22 Feb. 2006.

The selected microorganism to be used in a biocatalyst can be targeted to the sought activity. The biocatalysts thus often contain substantially pure strain types of microorganisms and, because of the targeting, enable high bioactivity to be achieved and provide a stable population of the microorganism in the biocatalyst.

Examples of microorganisms for sugar conversion include, but are not limited to, wild-type and modified microorganisms such as *Saccharomyces* cervisiae strains TMB 3400, TMB 3006, and 424A(LNF-ST), *Pachysolen tannophilus*, modified *E. coli* strains; and the like. See, U.S. Patent Application Publication 2010/0285552, hereby incorporated by reference. Examples of microorganisms capable of bioconverting pentose to ethanol include, but are not limited to, *Zymomonas mobilis, Pichia stipitis, Candida shehatae*, and *Pachysolen tannophilus*, and recombinant microorganisms such as, *Escherichia, Pseudomonas, Alcaligenes, Salmonella, Shigella, Burkholderia, Oligotropha, Klebsiella, Pichia, Candida, Hansenula, Saccharomyces, Kluyveromyces, Comamonas, Corynebacterium, Brevibacterium, Rhodococcus, Azotobacter, Citrobacter, Enterobacter, Clostridium, Lactobacillus, Aspergillus, Zygosaccharomyces, Dunaliella, Debaryomyces, Mucor, Torulopsis, Methylobacteria, Bacillus, Rhizobium* and *Streptomyces* as are known in the art. See, for instance, Aristidou, et al., Conversion of Renewable Resources to Biofuels and Fine Chemicals: Current Trends and Future Prospects, in Fermentation Microbiology and Biotechnology, 2011, Third Edition, pp 225 to 261. Other biocatalysts include those effective for the bioconversion of hexoses, or can bioconvert one or more other components in the thin stillage such as acetic acid (e.g., *Geobacter sulfurreducens*), lactic acid and other metabolites (e.g., *Pediococcus, Lactobacillus, Enterococcus*, and *Bacillus*). Representative microorganisms for making biocatalysts to make organic compounds include, without limitation, those set forth in United States published patent application nos. 2011/0072714, especially paragraph 0122; 2010/0279354, especially paragraphs 0083 through 0089; 2011/0185017, especially paragraph 0046; 2009/0155873; especially paragraph 0093; and 20060063217, especially paragraphs 0030 and 0031. Other representative microorganisms include *Acidovorax delafieldi* P4-1, *Acinetobacter* sp. (*A. calcoaceticus*), *Alcaligenes* sp. (*A. dentrificans*), *Alloiococcus otitis, Ancylobacter aquaticus, Arthrobacter sulfurous, Arthrobacter* sp. (*A. protophormiae*), *Bacillus cereus, Beijerinckia* sp., *Brevibacterium* sp. HL4, *Brettanomyces* sp., *Campylobacter jejuni, Carboxydothermus hydrogenoformans, Cornynebacterium* sp. strain m15, *Corynebacterium* (*glutamicum*), *Corynebacterium efficiens, Deinococcus radiophilus, Dekkera bruxellensis, Enterococcus faecium, Enterococcus gallinarium, Enterococcus faecalis, Methylosinus trichosporum* OB3b, *Methylosporovibrio methanica* 812, *Methanosarcina* sp., *Methanomonas* sp., *Methanospirilium, Methanobacerium* sp., *Methanobacterium bryantii, Methylomonas* sp., *Methylosinus* sp., *Moorella* (*Clostridium*) *thermoacetica*), *Mycobacterium* sp. strain GP1 *Neptunomonas naphthovorans, Pachysolen* sp., *Pantoea, P. pavonaceae, Pseudomonas* ADP, *P. stutzeri, P. putida, Pseudomonas* Strain PS1, *P. cepacia* G4, *P. medocina* KR, *P. picketti* PK01, *P. vesicularis, P. paucimobilis, Pseudomonas* sp. DLC-P11, *P. mendocina, P. chichhori*, strain IST 103), *Schizochytriu* sp., *Sphingomonas* (*S. yanoikuyae,* S. sp. RW1), *Synechococcus* sp., *Synechocystis* sp., *Xanthobacter autotrophicus* GJ10, *X. flavus, Bacteroides succinogens, Butyrivibrio fibrisolvens, Clostridium cellobioparum, Ruminococcus albus, Ruminococcus flavefaciens, Eubacterium cellulosolvens, Clostridium cellulosolvens, Clostridium cellulovorans, Bacteroides cellulosolvens*, and *Acetivibrio cellulolyticus Gliricidia* sp., *Albizia* sp., *Parthenium* sp. *Cupriavidus basilensis, Cupriavidus campinensis, Cupriavidus gilardi, Cupriavidus laharsis, Cupriavidus metallidurans, Cupriavidus oxalaticus, Cupriavidus pauculus, Cupriavidus pinatubonensis, Cupriavidus respiraculi, Cupriavidus taiwanensis, Oligotropha carboxidovorans, Thiobacillus* sp., *Thiobacillus denitrificans, Thiobacillus thioxidans, Thiobacillus ferrooxidans, Thiobacillus concretivorus, Acidithiobacillus albertensis, Acidithiobacillus caldus, Acidithiobacillus cuprithermicus, Rhodopseudomonas palustris, Rhodobacter sphaeroides, Rhodopseudomonas capsulate, Rhodopseudomonas acidophila, Rhodopseudomonas viridis, Desulfotomaculum acetoxidans, Desulfotomaculum kuznetsovii, Desulfotomaculum nigrificans, Desulfotomaculum reducens, Desulfotomaculum carboxydivorans, Methanosarcina barkeri, Methanosarcina acetivorans, Moorella thermoacetica, Carboxydothermus hydrogenoformans, Rhodospirillum rubrum, Acetobacterium woodii, Butyribacterium methylotrophicum, Eubacterium limosum, Oxobacter pfennigii, Peptostreptococcus productus, Rhodopseudomonas palustris* P4, *Rubrivivax gelatinosus, Citrobacter* sp Y19, *Methanosarcina acetivorans* C2A, *Desulfosporosinus orientis, Desulfovibrio desulfuricans, Desulfovibrio vulgaris, Moorella thermoautotrophica, Carboxydibrachium pacificus, Carboxydocella thermoautotrophica, Thermincola carboxydiphila, Thermolithobacter carboxydivorans, Thermosinus carboxydivorans, Methanothermobacter thermoautotrophicus, Desulfotomaculum carboxydivorans, Desulfotomaculum kuznetsovii, Desulfotomaculum nigrificans, Desulfotomaculum thermobenzoicum* subsp. *thermosyntrophicum, Syntrophobacter fumaroxidans, Clostridium acidurici, Desulfovibrio africanus, C. pasteurianum, C. pasteurianum* DSM 525, *Paenibacillus polymyxa, Chloronema, Roseiflexus, Chlorobium, Clathrochloris, Nitrosolobus* sp., *Nitrosovibrio* sp., *Siderococcus* sp., *Methanobrevibacter* sp., *Arabidopsis thaliana, Panicum virgatum, Miscanthus giganteus*, and *Zea mays* (plants), *Chlamydomonas reinhardtii* and *Dunaliela salina* (algae), *Synechococcus* sp PCC 7002, *Synechococcus* sp. PCC 7942, *Synechocystis* sp. PCC 6803, *Thermosynechococcus elongatus* BP-1 (cyanobacteria), *Chlorobium tepidum* (green sulfur bacteria), *Chloroflexus auranticus* (green non-sulfur bacteria), *Chromatium tepidum* and *Chromatium vinosum* (purple sulfur bacteria), *Rhodospirillum rubrum, Rhodobacter capsulatus*, and *Rhodopseudomonas palusris* (purple non-sulfur bacteria).

Photosynthetic microorganisms include bacteria, algae, yeasts and molds having biocatalytic activity activated by light radiation. Examples of photosynthetic microorganisms for higher oxygenated organic compound production include, but are not limited to alga such as Bacillariophyceae strains, Chlorophyceae, Cyanophyceae, Xanthophyceaei, Chrysophyceae, *Chlorella* (e.g., *Chlorella protothecoides*), *Crypthecodinium, Schizocytrium, Nannochloropsis, Ulkenia, Dunaliella, Cyclotella, Navicula, Nitzschia, Cyclotella, Phaeodactylum*, and *Thaustochytrids*; yeasts such as *Rhodotorula, Saccharomyces*, and *Apiotrichum* strains; and fungi species such as the *Mortierella* strain. Genetically enhanced photoautotrophic cyanobacteria, algae, and other photoautotrophic organisms have been adapted to bioconvert carbohydrates internal to the microorganism directly to ethanol, butanol, pentanol and other higher alcohols and other biofuels. For example, genetically modified cyanobacteria having constructs comprising DNA fragments encoding pyruvate decarboxylase (pdc) and alcohol dehydrogenase (adh) enzymes are described in U.S. Pat. No. 6,699,696. Cyanobacteria are photosynthetic bacteria which require light, inorganic elements, water, and a carbon source, generally carbon dioxide, to metabolize and grow. The production of ethanol using genetically engineered cyanobacteria has also been described in PCT Published Patent Application WO 2007/084477.

It is claimed:

1. A process for producing ethanol by the fermentation of biomass containing carbohydrate comprising:
   a. hydrolyzing an admixture of water, enzyme and biomass under hydrolyzing conditions sufficient to convert carbohydrate by enzymatic hydrolysis and provide a hydrolysate containing pentose and hexose;
   b. subjecting at least a portion of the hydrolysate of step (a) to fermentation conditions sufficient to convert at least a portion of the hexose to ethanol to provide an ethanol-containing fermentation broth containing solids and pentose, said fermentation conditions comprising the presence of microorganism capable of converting hexose to ethanol, and said ethanol-containing fermentation broth containing solids;
   c. fractionating by distillation at least a portion of the ethanol-containing fermentation broth of step (b) to provide an ethanol product fraction and a whole stillage containing water, solids and unfermented sugars comprising pentose;
   d. separating at least a portion of the whole stillage of step (c) to provide a thin stillage containing pentose and having an essential absence of solids and to provide a solids-containing fraction;
   e. contacting under fermentation conditions in a fermentation zone at least a portion of the thin stillage of step (d) with biocatalyst said biocatalyst comprising:
      i. a solid structure of hydrated hydrophilic polymer defining an interior structure having a plurality of interconnected major cavities having a smallest dimension of between about 5 and 100 microns and a Hydration Expansion Volume (HEV), which is calculated in volume percent, of about 1000 or more, and
      ii. a population of microorganisms capable of converting pentose to ethanol substantially irreversibly retained in the interior of the solid structure, said population of microorganisms being in a concentration of about 60 grams per liter or more based upon the volume defined by the exterior of the solid structure when fully hydrated, to provide a treated thin stillage having a reduced pentose content and substantially no solids;
   f. withdrawing the treated thin stillage from the fermentation zone of step (e) while retaining the biocatalyst in the fermentation zone;
   g. evaporating water and ethanol from at least a portion of the treated thin stillage of step (f) to provide a concentrated solubles product and vapor; and
   h. passing at least a portion of the evaporated water and ethanol of step (g) to step (a).

2. The process of claim 1 wherein the fermentation of step (b) produces metabolites in addition to ethanol, the fermentation of step (e) converts at least a portion of the metabolites, and an aliquot portion of the treated thin stillage of step (e) is passed to step (a).

3. The process of claim 1 wherein the evaporating of step (g) is conducted in at least two effects, and vapor from at least the first effect is passed to the fractionation of step (c), and vapor from at least the last effect is passed to step (a).

4. The process of claim 1, wherein the thin stillage of step (d) comprises fermentable sugars in a concentration between about 10 and 50 grams per liter.

5. The process of claim 1, wherein the thin stillage of step (d) comprises fermentable sugars in a concentration between about 3 and 40 grams per liter.

* * * * *